US007559932B2

(12) United States Patent
Truckai et al.

(10) Patent No.: US 7,559,932 B2
(45) Date of Patent: Jul. 14, 2009

(54) BONE TREATMENT SYSTEMS AND METHODS

(75) Inventors: Csaba Truckai, Saratoga, CA (US);
John H. Shadduck, Tiburon, CA (US);
Robert Luzzi, Pleasanton, CA (US);
Grace A. Carlson, San Francisco, CA (US); C. Travis Rappleye, San Jose, CA (US)

(73) Assignee: Dfine, Inc., San Jose, CA (US)

( * ) Notice: Subject to any disclaimer, the term of this patent is extended or adjusted under 35 U.S.C. 154(b) by 402 days.

(21) Appl. No.: 11/165,652

(22) Filed: Jun. 24, 2005

(65) Prior Publication Data

US 2006/0122623 A1    Jun. 8, 2006

Related U.S. Application Data

(60) Provisional application No. 60/633,509, filed on Dec. 6, 2004.

(51) Int. Cl.
*A61B 17/00* (2006.01)
(52) U.S. Cl. ................... 606/92; 606/93; 623/17.11
(58) Field of Classification Search ........... 606/92–94; 623/17.11–17.16, 23.19, 23.62
See application file for complete search history.

(56) References Cited

U.S. PATENT DOCUMENTS 3,349,840 A    10/1967    Tope et al.

(Continued)

FOREIGN PATENT DOCUMENTS

WO    WO 02/058592    8/2002

(Continued)

OTHER PUBLICATIONS

Furderer S, Anders M. Schwindling B, Salick M, Duber C, Wenda K, Urban R, Gluck M, Eysel P., "Verterbral body stenting. A method for repositioning and augmenting vertebral compression fractures", Orthopade. Apr. 2002; 31(4):356-61, Abstract.

(Continued)

*Primary Examiner*—Eduardo C Robert
*Assistant Examiner*—Tara R George
(74) *Attorney, Agent, or Firm*—Knobbe, Martens, Olson & Bear, LLP

(57) ABSTRACT

The present invention relates in certain embodiments to medical devices for treating osteoplasty procedures such as vertebral compression fractures. More particularly, embodiments of the invention relate to instruments and methods for controllably restoring vertebral body height by controlling the geometry of fill material introduced into cancellous bone. An exemplary system utilizes Rf energy in combination a conductive bone fill material for polymerizing the surface of the inflow plume to control the geometry of the fill material and the application of force caused by inflows of fill material. In another embodiment, method of treating bone includes injecting a volume of fill material into a bone and selectively modifying a viscosity of a selected portion of the bone filler to control the direction of flow of the fill material within the bone. A system for treating bone using this method includes an introducer for delivering fill material into the bone and an energy source selectively coupleable to the fill material to alter the viscosity of the fill material as it flows out of the introducer.

51 Claims, 18 Drawing Sheets

U.S. PATENT DOCUMENTS

| | | | |
|---|---|---|---|
| 4,265,618 A * | 5/1981 | Herskovitz et al. | 433/32 |
| 4,280,233 A | 7/1981 | Raab | |
| 4,294,251 A | 10/1981 | Greenwald et al. | |
| 4,338,925 A | 7/1982 | Miller | |
| 4,735,625 A | 4/1988 | Davidson | |
| 4,772,287 A * | 9/1988 | Ray et al. | 623/17.12 |
| 4,959,104 A | 9/1990 | Iino et al. | |
| 4,963,151 A | 10/1990 | Ducheyne et al. | |
| 4,969,888 A | 11/1990 | Scholten et al. | |
| 4,969,906 A | 11/1990 | Kronman | |
| 5,037,437 A | 8/1991 | Matsen | |
| 5,051,482 A | 9/1991 | Tepic | |
| 5,108,404 A | 4/1992 | Scholten | |
| 5,431,654 A | 7/1995 | Nic | |
| 5,514,135 A | 5/1996 | Earle | |
| 5,542,928 A | 8/1996 | Evans et al. | |
| 5,574,075 A | 11/1996 | Draemert | |
| 5,679,299 A | 10/1997 | Gilbert et al. | |
| 5,693,099 A | 12/1997 | Harle | |
| 5,814,681 A | 9/1998 | Hino et al. | |
| 6,048,346 A | 4/2000 | Reiley | |
| 6,171,312 B1 | 1/2001 | Beaty | |
| 6,231,615 B1 | 5/2001 | Preissman | |
| 6,235,043 B1 | 5/2001 | Reiley et al. | |
| 6,236,020 B1 | 5/2001 | Friedman | |
| 6,241,734 B1 | 6/2001 | Scribner | |
| 6,248,110 B1 | 6/2001 | Reiley et al. | |
| 6,261,289 B1 | 7/2001 | Levy | |
| 6,264,659 B1 | 7/2001 | Ross et al. | |
| 6,280,456 B1 | 8/2001 | Scribner et al. | |
| 6,309,420 B1 | 10/2001 | Preissman | |
| 6,312,254 B1 * | 11/2001 | Friedman | 433/32 |
| 6,316,885 B1 | 11/2001 | Collins et al. | |
| 6,319,255 B1 | 11/2001 | Grundei et al. | |
| 6,332,894 B1 | 12/2001 | Stalcup et al. | |
| 6,358,254 B1 | 3/2002 | Anderson | |
| 6,395,007 B1 * | 5/2002 | Bhatnagar et al. | 606/94 |
| 6,425,923 B1 | 7/2002 | Stalcup et al. | |
| 6,436,143 B1 * | 8/2002 | Ross et al. | 623/17.16 |
| 6,439,439 B1 | 8/2002 | Rickard | |
| 6,443,988 B2 | 9/2002 | Felt et al. | |
| 6,447,514 B1 | 9/2002 | Stalcup et al. | |
| 6,458,127 B1 | 10/2002 | Truckai et al. | |
| 6,485,436 B1 | 11/2002 | Truckai | |
| 6,524,102 B2 * | 2/2003 | Davis | 433/32 |
| 6,610,079 B1 * | 8/2003 | Li et al. | 606/232 |
| 6,676,664 B1 | 1/2004 | Al-Assir | |
| 6,706,069 B2 | 3/2004 | Berger | |
| 6,709,149 B1 | 3/2004 | Tepic | |
| 6,712,852 B1 | 3/2004 | Chung et al. | |
| 6,719,773 B1 | 4/2004 | Boucher et al. | |
| 6,723,095 B2 | 4/2004 | Hammerslag | |
| 6,726,691 B2 * | 4/2004 | Osorio et al. | 606/94 |
| 6,740,093 B2 | 5/2004 | Hochschuler et al. | |
| 6,767,936 B2 | 7/2004 | Walz et al. | |
| 6,783,515 B1 | 8/2004 | Miller | |
| 6,814,736 B2 | 11/2004 | Reiley et al. | |
| 6,929,640 B1 | 8/2005 | Underwood | |
| 6,958,061 B2 | 10/2005 | Truckai et al. | |
| 6,979,352 B2 * | 12/2005 | Reynolds | 623/17.11 |
| 6,985,061 B2 | 1/2006 | Hafskjold et al. | |
| 7,044,954 B2 | 5/2006 | Reiley | |
| 7,115,163 B2 | 10/2006 | Zimmerman | |
| 7,153,306 B2 | 12/2006 | Ralph et al. | |
| 7,153,307 B2 * | 12/2006 | Scribner et al. | 606/93 |
| 7,160,020 B2 | 1/2007 | Sand | |
| 7,273,523 B2 | 9/2007 | Wenz | |
| 2001/0011190 A1 | 8/2001 | Park | |
| 2001/0012968 A1 | 8/2001 | Preissman | |
| 2002/0026195 A1 | 2/2002 | Layne et al. | |
| 2002/0082608 A1 | 6/2002 | Reiley et al. | |
| 2002/0099385 A1 | 7/2002 | Ralph et al. | |
| 2002/0147497 A1 | 10/2002 | Belef et al. | |
| 2002/0156483 A1 | 10/2002 | Voellmicke et al. | |
| 2002/0161373 A1 | 10/2002 | Osorio et al. | |
| 2003/0012080 A1 | 1/2003 | Coffeen et al. | |
| 2003/0032733 A1 | 2/2003 | Fischer et al. | |
| 2003/0032929 A1 | 2/2003 | McGuckin | |
| 2003/0130373 A1 | 7/2003 | Walz et al. | |
| 2003/0130738 A1 | 7/2003 | Hovda et al. | |
| 2003/0171748 A1 | 9/2003 | Truckai et al. | |
| 2003/0208192 A1 | 11/2003 | Truckai et al. | |
| 2003/0220648 A1 | 11/2003 | Osorio et al. | |
| 2003/0233096 A1 | 12/2003 | Osorio et al. | |
| 2004/0006347 A1 | 1/2004 | Sproul | |
| 2004/0024410 A1 | 2/2004 | Olson | |
| 2004/0073308 A1 | 4/2004 | Kuslich et al. | |
| 2004/0083002 A1 | 4/2004 | Belef et al. | |
| 2004/0092948 A1 | 5/2004 | Stevens et al. | |
| 2004/0102845 A1 | 5/2004 | Reynolds | |
| 2004/0110285 A1 | 6/2004 | Lendlein | |
| 2004/0138748 A1 | 7/2004 | Boyer, II et al. | |
| 2004/0167561 A1 | 8/2004 | Boucher et al. | |
| 2004/0186576 A1 * | 9/2004 | Biscup et al. | 623/17.12 |
| 2004/0193171 A1 | 9/2004 | DiMauro et al. | |
| 2004/0225296 A1 | 11/2004 | Reiss et al. | |
| 2004/0225926 A1 | 11/2004 | Scales et al. | |
| 2004/0228898 A1 | 11/2004 | Ross et al. | |
| 2004/0267271 A9 | 12/2004 | Scribner et al. | |
| 2004/0267272 A1 | 12/2004 | Henniges | |
| 2005/0010231 A1 | 1/2005 | Myers | |
| 2005/0015148 A1 | 1/2005 | Jansen et al. | |
| 2005/0059979 A1 | 3/2005 | Yetkinler | |
| 2005/0119650 A1 | 6/2005 | Sanders et al. | |
| 2005/0180806 A1 | 8/2005 | Green et al. | |
| 2005/0209595 A1 | 9/2005 | Karmon | |
| 2005/0222681 A1 | 10/2005 | Richley et al. | |
| 2005/0245938 A1 | 11/2005 | Kochan | |
| 2005/0251149 A1 * | 11/2005 | Wenz | 606/94 |
| 2006/0052743 A1 | 3/2006 | Reynolds | |
| 2006/0052794 A1 | 3/2006 | McGill et al. | |
| 2006/0074433 A1 | 4/2006 | McGill et al. | |
| 2006/0079905 A1 | 4/2006 | Beyar et al. | |
| 2006/0095138 A1 | 5/2006 | Truckai et al. | |
| 2006/0100635 A1 | 5/2006 | Reiley et al. | |
| 2006/0122614 A1 | 6/2006 | Truckai et al. | |
| 2006/0122621 A1 | 6/2006 | Truckai et al. | |
| 2006/0122622 A1 | 6/2006 | Truckai et al. | |
| 2006/0122624 A1 | 6/2006 | Truckai et al. | |
| 2006/0122625 A1 | 6/2006 | Truckai et al. | |
| 2007/0022912 A1 | 2/2007 | Zimmermann | |
| 2007/0118144 A1 | 5/2007 | Truckai et al. | |
| 2007/0162043 A1 | 7/2007 | Truckai et al. | |
| 2007/0191858 A1 | 8/2007 | Truckai et al. | |
| 2007/0191964 A1 | 8/2007 | Preissman | |
| 2007/0233148 A1 | 10/2007 | Truckai et al. | |

FOREIGN PATENT DOCUMENTS

| | | |
|---|---|---|
| WO | WO 02/087416 | 11/2002 |
| WO | WO 2006/031490 | 3/2006 |

OTHER PUBLICATIONS

International Search Report, mailing date May 31, 2006, PCT/US2005/044055, 4 pg.

International Search Report, mailing date Jun. 20, 2006, PCT/US2005/043984, 2 pg.

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

U.S. Appl. No. 11/469,769, filed Sep. 1, 2006, Truckai et al.

U.S. Appl. No. 11/469,752, filed Sep. 1, 2006, Truckai et al.

Office action in U.S. Appl. No. 11/165,651, mailed Sep. 21, 2007.

Office Action in U.S. Appl. No. 11/148,973, mailed Jun. 29, 2007.
Office Action in U.S. Appl. No. 11/148,973, mailed Feb. 28, 2008.
Office Action in U.S. Appl. No. 11/165,651, mailed Mar. 24, 2008.
Office Action in U.S. Appl. No. 11/165,045, mailed Mar. 26, 2008.
Office Action in U.S. Appl. No. 11/196,089, mailed Jan. 3, 2008.
Office Action in U.S. Appl. No. 11/208,448, mailed Nov. 30, 2007.
Office Action in U.S. Appl. No. 11/209,035, mailed Jan. 3, 2008.
Pending Claims in the Amendment in response to non-final Office Action mailed Sep. 22, 2008 in U.S. Appl. No. 11/165,651.

* cited by examiner

BONE TREATMENT SYSTEMS AND METHODS

CROSS-REFERENCE TO RELATED APPLICATIONS

This application claims the benefit of Provisional U.S. Patent Application Ser. No. 60/633,509 filed Dec. 6, 2004, titled Bone Fill Materials and Methods of Use for Treating Vertebral Fractures the entire contents of which are incorporated herein by reference and should be considered a part of this specification. This application is also related to U.S. patent application Ser. No. 11/165,651, filed Jun. 24, 2005, titled Bone Treatment Systems and Methods, the entire contents of which are hereby incorporated by reference and should be considered a part of this specification.

BACKGROUND OF THE INVENTION

1. Field of the Invention

The present invention relates in certain embodiments to medical devices for treating osteoplasty procedures such as vertebral compression fractures. More particularly, embodiments of the invention relate to instruments and methods for controllably restoring vertebral body height by controlling the geometry of fill material introduced into cancellous bone. An exemplary system utilizes Rf energy in combination a conductive bone fill material for polymerizing the surface of the inflow plume to control the geometry of the fill material and the application of force caused by inflows of fill material.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebra is identified under fluoroscopy. A needle is introduced into the vertebral body under fluoroscopic control, to allow direct visualization. A bilateral transpedicular (through the pedicle of the vertebra) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no= 0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon applies also compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide systems and methods for use in treatment of vertebral compression fractures that provide a greater degree of control over introduction of bone support material, and that provide better outcomes. The present invention meets this need and provides several other advantages in a novel and nonobvious manner.

SUMMARY OF THE INVENTION

Certain embodiments of the invention provide systems and methods for utilizing Rf energy in combination with a bone fill material that carries an electrically conductive filler for polymerizing surface portions of the inflow plume to thereby control the direction of flow and the ultimate geometry of a flowable, in-situ hardenable composite. The system and method further includes means for sealing tissue in the interior of a vertebra to prevent migration of monomers, fat or emboli into the patient's bloodstream.

In accordance with one embodiment, a method for treating bone is provided. The method comprises introducing an infill material into an interior region of a bone and contemporaneously applying energy from an energy source as the infill material is introduced to selectively alter a flowability property of the infill material.

In accordance with another embodiment, a method for treating bone is provided. The method comprises providing a bone fill material including a composition that has at least one of an energy-absorbing property and an energy-transmitting property. The method also comprises introducing a volume of the fill material into an interior of a bone member and applying energy from a remote energy source to the composition, wherein the energy-absorbing or energy-transmitting property thereby causes a thermal modification in at least one of the fill material and adjacent portions of the interior of the bone member.

In accordance with another embodiment, a method for treating bone is provided comprising introducing at least one instrument working end into an interior region of a bone member. The method also comprises introducing an infill material into the interior region of the bone member and applying energy from an energy source through the at least one working end to the fill material to seal tissue about the surface of the fill material, wherein the sealed tissue prevents migration of emboli into the a blood stream.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

Figure 1:
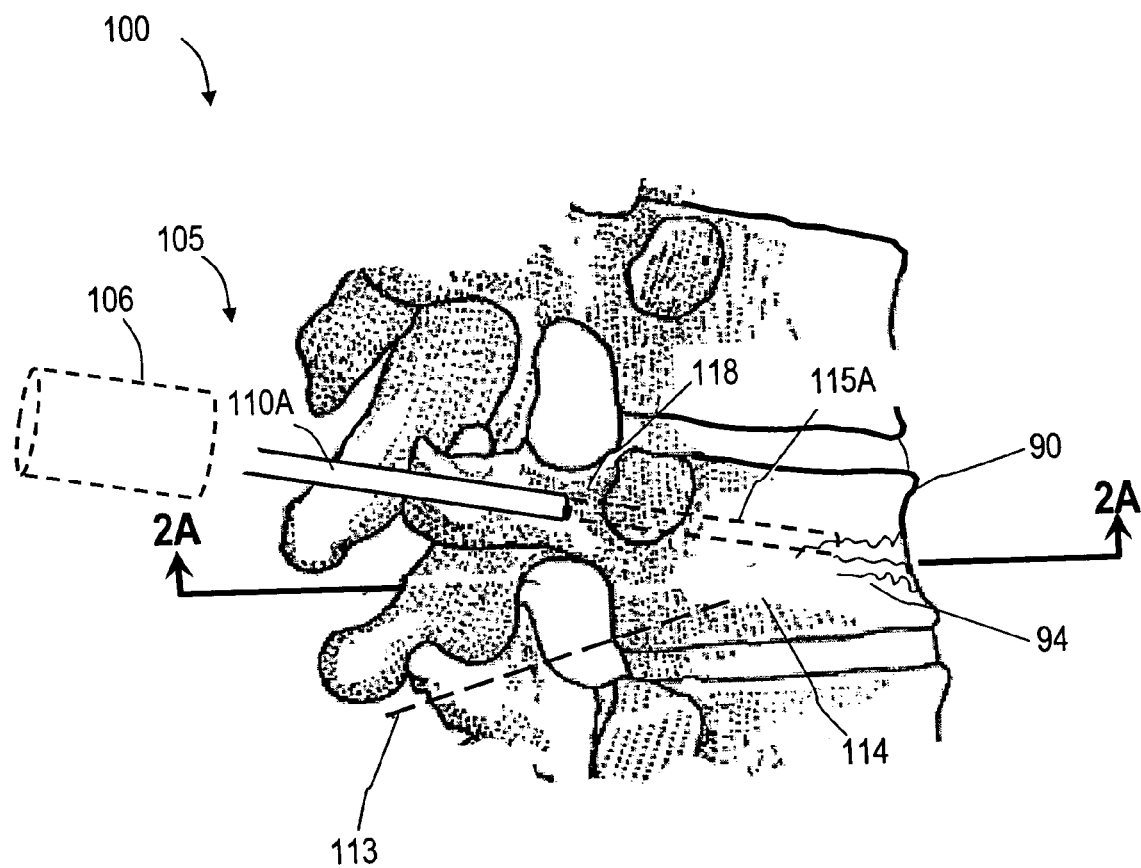
FIG. 1 is a schematic side view of a spine segment showing a vertebra with a compression fracture and an introducer, in accordance with one embodiment disclosed herein.

FIG. 1 illustrates one embodiment of the invention in treating a spine segment in which a vertebral body 90 has a wedge compression fracture indicated at 94. In one embodiment, the systems and methods of the invention are directed to safely introducing a bone fill material into cancellous bone of the vertebra without extravasation of fill material in unwanted directions (i) to prevent micromotion in the fracture for eliminating pain, and (ii) to support the vertebra and increase vertebral body height. Further, the invention includes systems and methods for sealing cancellous bone (e.g., blood vessels, fatty tissues etc.) in order to prevent monomers, fat, fill material and other emboli from entering the venous system during treatment.

Figure 2A:
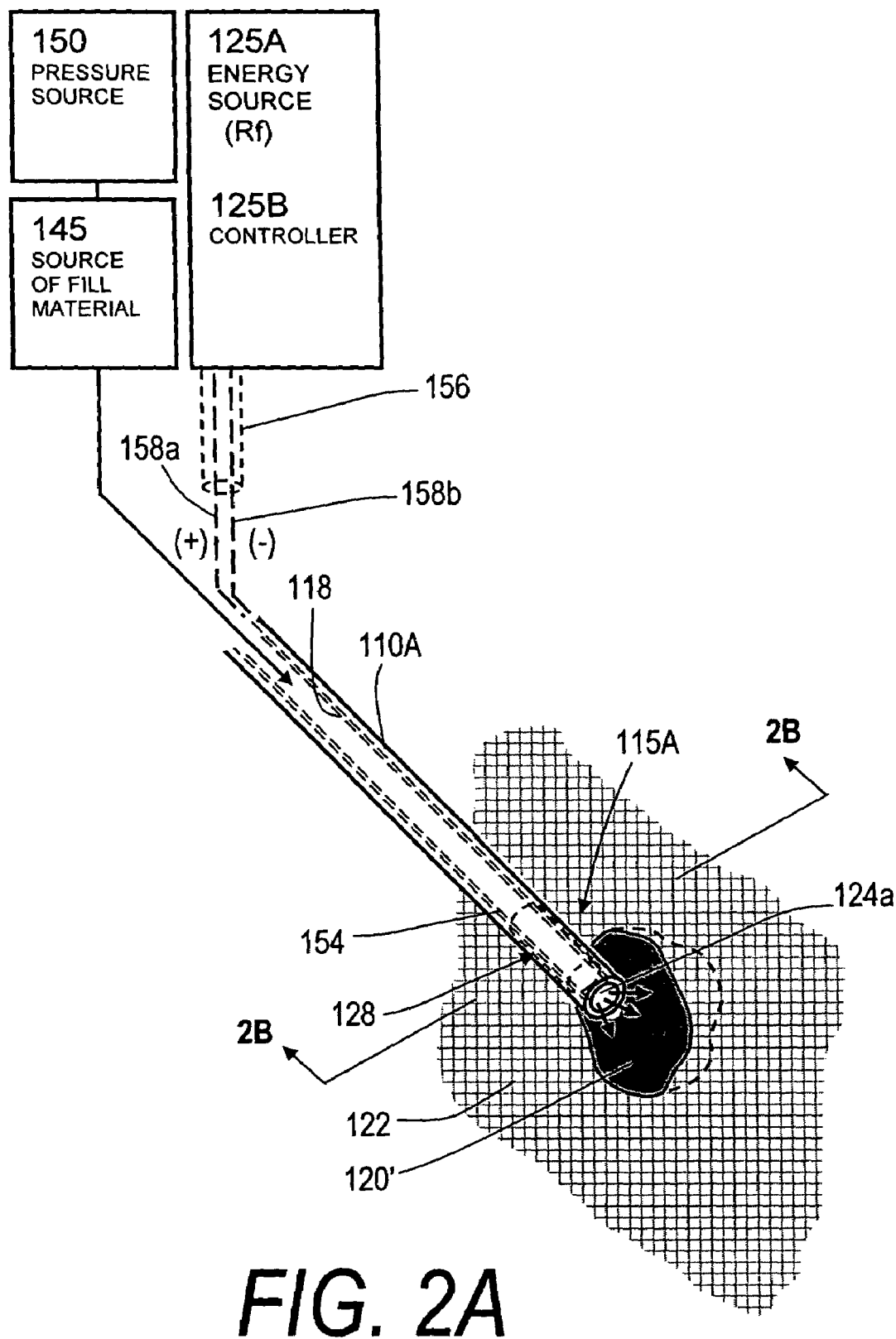
FIG. 2A is a schematic perspective view of a system for treating bone, in accordance with one embodiment.

FIG. 1 illustrates a fractured vertebra and bone infill system 100 which includes a probe 105 having a handle end 106 extending to an elongated introducer 110A and a working end 115A, shown in FIG. 2A. The introducer is shown introduced through pedicle 118 of the vertebra for accessing the osteoporotic cancellous bone 122 (See FIG. 2A). The initial aspects of the procedure are similar to conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the introducer 110A is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

It should be appreciated that the introducer 110A also can be introduced into the vertebra from other angles, for example, along axis 113 through the wall of the vertebral body 114 as in FIG. 1 or in an anterior approach (not shown). Further, first and second cooperating introducers can be used in a bilateral transpedicular approach. Additionally, any mechanism known in the art for creating an access opening into the interior of the vertebral body 90 can be used, including open surgical procedures.

DEFINITIONS

"Bone fill material, infill material or composition" includes its ordinary meaning and is defined as any material for infilling a bone that includes an in-situ hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

An "elastomer" includes its ordinary meaning and is defined as material having to some extent the elastic properties of natural rubber wherein the material resumes or moves toward an original shape when a deforming force is removed.

"Substantially" or "substantial" mean largely but not entirely. For example, substantially may mean about 10% to about 99.999%, about 25% to about 99.999% or about 50% to about 99.999%.

"Osteoplasty" includes its ordinary meaning and means any procedure wherein fill material is delivered into the interior of a bone.

"Vertebroplasty" includes its ordinary meaning and means any procedure wherein fill material is delivered into the interior of a vertebra.

Figure 2B:
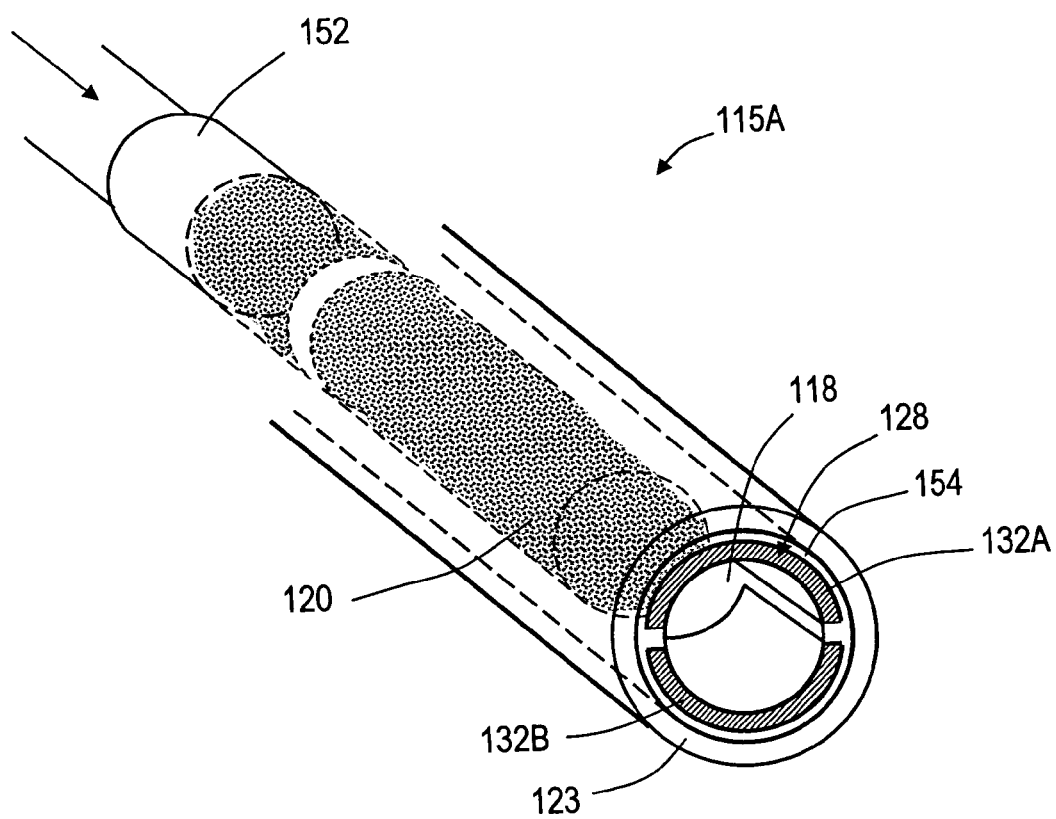
FIG. 2B is a schematic perspective sectional view of a working end of the introducer taken along line 2B-2B of FIG. 2A.
Figure 3A:
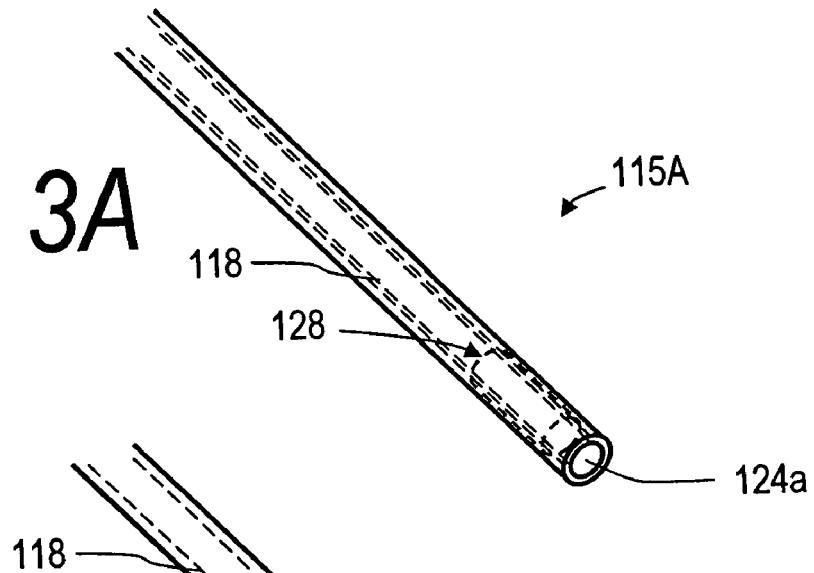
FIG. 3A is a schematic perspective view of a working end of a probe, in accordance with one embodiment.
Figure 3B:
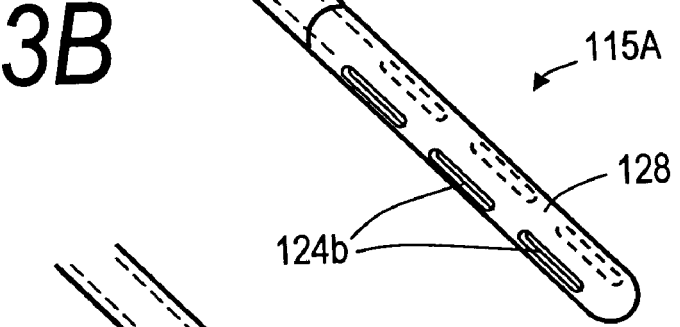
FIG. 3B is a schematic perspective view of a working end of a probe, in accordance with another embodiment.
Figure 3C:
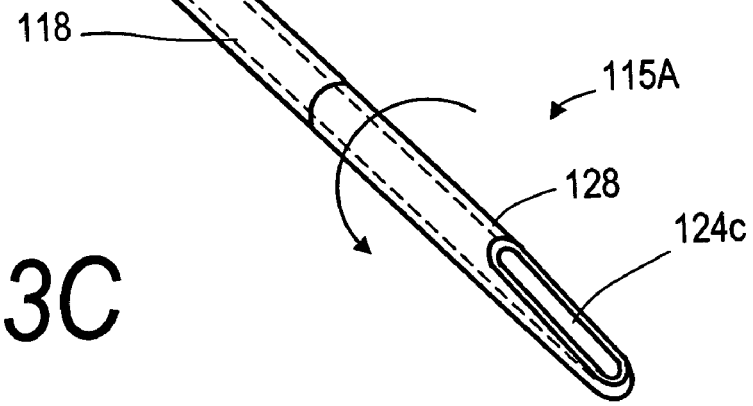
FIG. 3C is a schematic perspective view of a working end of a probe, in accordance with yet another embodiment.

Now referring to FIGS. 2A and 2B, the end of introducer 110A is shown schematically after being introduced into cancellous bone 122 with an inflow of fill material indicated at 120. The cancellous bone can be in any bone, for example in a vertebra. It can be seen that the introducer 110A and working end 115A comprise a sleeve or shaft that is preferably fabricated of a metal having a flow channel 118 extending therethrough from the proximal handle end 106 (see FIG. 1). In one embodiment, the introducer shaft is a stainless steel tube 123 having an outside diameter ranging between about 3.5 and 4.5 mm, but other dimensions are possible. As can be seen in FIG. 2A and 3A, the flow channel 118 can terminate in a single distal open termination or outlet 124a in the working end 115A, or there can be a plurality of flow outlets or ports 124b configured angularly about the radially outward surfaces of the working end 115A of FIG. 3B. The outlets in the working end thus allow for distal or radial ejection of fill material, or a working end can have a combination of radial and distal end outlets. As can be seen in FIG. 3C, the distal end of working end 115A also can provide an angled distal end outlet 124c for directing the flow of fill material from the outlet by rotating the working end.

In FIGS. 2A and 2B, it can be seen that system 100 includes a remote energy source 125A and controller 125B that are operatively coupled to an energy emitter 128 in working end 115A for applying energy to fill material 120 contemporaneous with and subsequent to ejection of the fill material from the working end. As shown in FIG. 2A, a preferred energy source 125A is a radiofrequency (Rf) source known in the art that is connected to at least one electrode (132a and 132b in FIGS. 2A and 2B) in contact with injected fill material 120 that carries a radiosensitive composition therein. It is equally possible to use other remote energy sources and emitters 128 in the working end which fall within the scope of the invention, such as (i) an electrical source coupled to a resistive heating element in the working end, (ii) a light energy source (coherent or broadband) coupled to an optical fiber or other light channel terminating in the working end; (iii) an ultrasound source coupled to an emitter in the working end; or (iv) a microwave source coupled to an antenna in the working end. In still another embodiment, the energy source can be a magnetic source. The fill material is configured with an energy-absorbing material or an energy-transmitting material that cooperates with energy delivery from a selected energy source. For example, the energy-absorbing or energy-transmitting material can be a radiosensitive or conductive material for cooperating with an Rf source, chromophores for cooperating with a light source, ferromagnetic particles for cooperating with a magnetic source, and the like.

As can be understood from FIGS. 2A and 2B, the exemplary introducer 110A is operatively coupleable to a source 145 of bone fill material 120 together with a pressure source or mechanism 150 that operates on the source of fill material to deliver the fill material 120 through the introducer 110A into a bone (see arrows). The pressure source 150 can comprise any type of pump mechanism, such as a piston pump or screw pump. In FIG. 2B, the pump mechanism is shown as a piston or plunger 152 that is slideable in channel 118 of introducer 110A.

As shown in FIGS. 2A and 2B, the introducer 110A preferably has an electrically and thermally insulative interior sleeve 154 that defines interior flow channel 118. The sleeve can be any suitable polymer known in the art such as PEEK, Teflon™ or a polyimide. As can be seen in FIG. 2B, interior sleeve 154 carries conductive surfaces that function as energy emitter 128, and more particularly comprise spaced apart opposing polarity electrodes 132a and 132b. The electrodes 132a and 132b can have any spaced apart configuration and are disposed about the distal termination of channel 118 or about the surfaces of outlet 124a. The electrode configuration alternatively can include a first electrode in the interior of channel 118 and a second electrode on an exterior of introducer 110A. For example, the metallic sleeve 123 or a distal portion thereof can comprise one electrode. In a preferred embodiment, the electrodes 132a and 132b are connected to Rf energy source 125A and controller 125B by electrical cable 156 with (+) and (−) electrical leads 158a and 158b therein that extend through the insulative sleeve 154 to the opposing polarity electrodes. In one embodiment, the electrical cable 156 is detachably coupled to the handle end 106 of probe 105 by male-female plug (not shown). The electrodes 132a and 132b can be fabricated of any suitable materials known to those skilled in the art, such as stainless steels, nickel-titanium alloys and alloys of gold, silver platinum and the like.

In one embodiment, not shown, the working end 115A can also carry any suitable thermocouple or temperature sensor for providing data to controller 125B relating to the temperature of the fill material 120 during energy delivery. One or more thermocouples may be positioned at the distal tip of the introducer, or along an outer surface of the introducer and spaced from the distal end, in order to provide temperature readings at different locations within the bone. The thermocouple may also be slideable along the length of the introducer. In another embodiment, the working end can have at least one side port (not shown) in communication with a coolant source, the port configured to provide the coolant (e.g., saline) therethrough into the cancellous bone 122 to cool the cancellous bone in response to a temperature reading from the temperature sensor.

Figure 4:
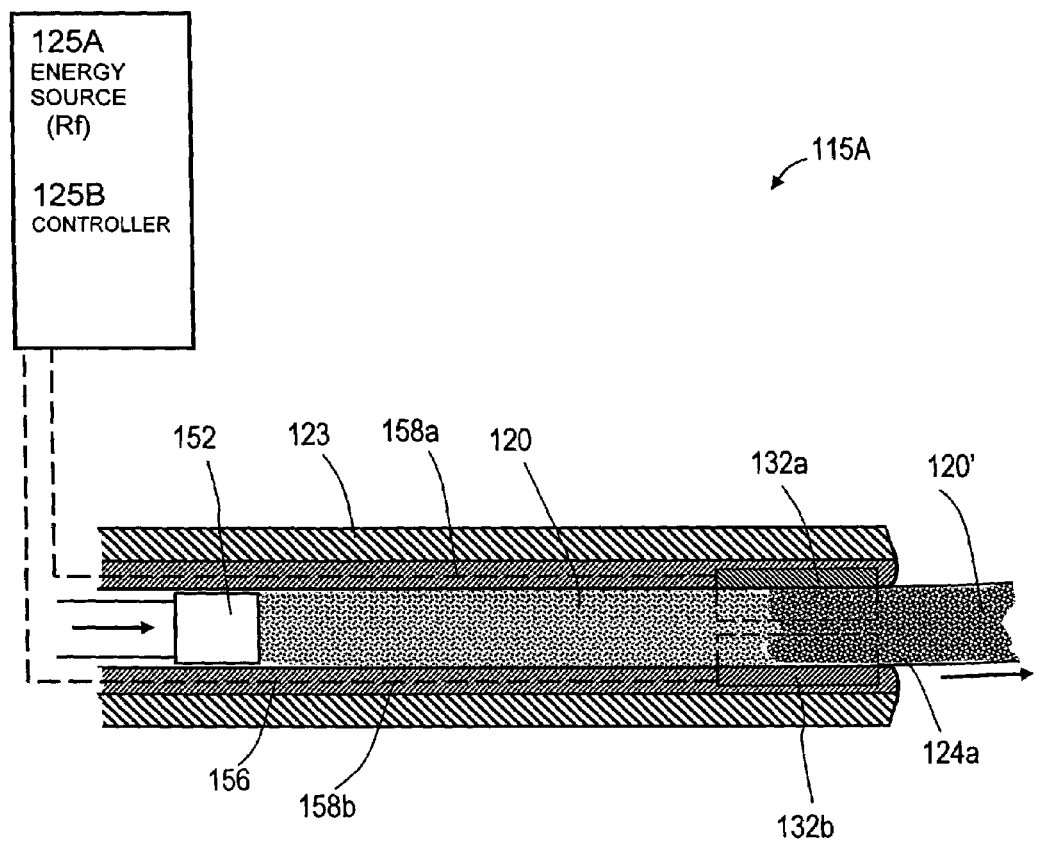
FIG. 4 is a schematic sectional side view of one embodiment of a working end of a probe, in accordance with one embodiment.

Now turning to FIG. 4, the sectional view of working end 115A illustrates the application of energy to fill material 120 as it is being ejected from outlet 124a. The fill material 120 in the proximal portion of channel 118 can be a low viscosity flowable material such as a two-part curable polymer that has been mixed (e.g., PMMA) but without any polymerization, for example, having a viscosity of less than about 50,000 cps. Such a low viscosity fill material allows for simplified lower pressure injection through introducer 110A. Further, the system allows the use of a low viscosity fill material 120 which can save a great deal of time for the physician.

In a preferred embodiment, it is no longer necessary to wait for the bone cement to partly polymerize before injection. As depicted in FIG. 4, energy delivery at selected parameters from electrodes 132a and 132b to fill material 120 contemporaneous with its ejection from outlet 124a selectively alters a property of fill material indicated at 120'. In one embodiment, the altered flow property is viscosity. For example, the viscosity of the fill material 120' can be increased to a higher viscosity ranging from about 100,000 cps or more, 1,000,000 cps or more, to 2,000,000 cps or more. In another embodiment, the flow property is Young's modulus. For example, the Young's modulus of the fill material 120' can be altered to be between about 10 kPa and about 10 GPa. In still another embodiment, the flow property can be one of durometer, hardness and compliance.

Preferably, the fill material carries a radiosensitive composition for cooperating with the Rf source 125A, as further described below. At a predetermined fill material flow rate and at selected Rf energy delivery parameters, the altered fill material 120' after ejection can comprise an elastomer. At yet another predetermined fill material flow rate and at other Rf energy delivery parameters, the altered fill material 120' after ejection can comprise a substantially solid material. In the system embodiment utilized for vertebroplasty as depicted in FIGS. 2A and 5B, the controller is adapted for delivering Rf energy contemporaneous with the selected flow rate of fill material to provide a substantially high viscosity fill material that is still capable of permeating cancellous bone. In other osteoplasty procedures such as treating necrosis of a bone, the system controller 125B can be adapted to provide much harder fill material 120' upon ejection from outlet 124a. Further, the system can be adapted to apply Rf energy to the fill material continuously, or in a pulse mode or in any selected intervals based on flow rate, presets, or in response to feedback from temperature sensors, impedance measurements or other suitable signals known to those skilled in the art.

Figure 5A:
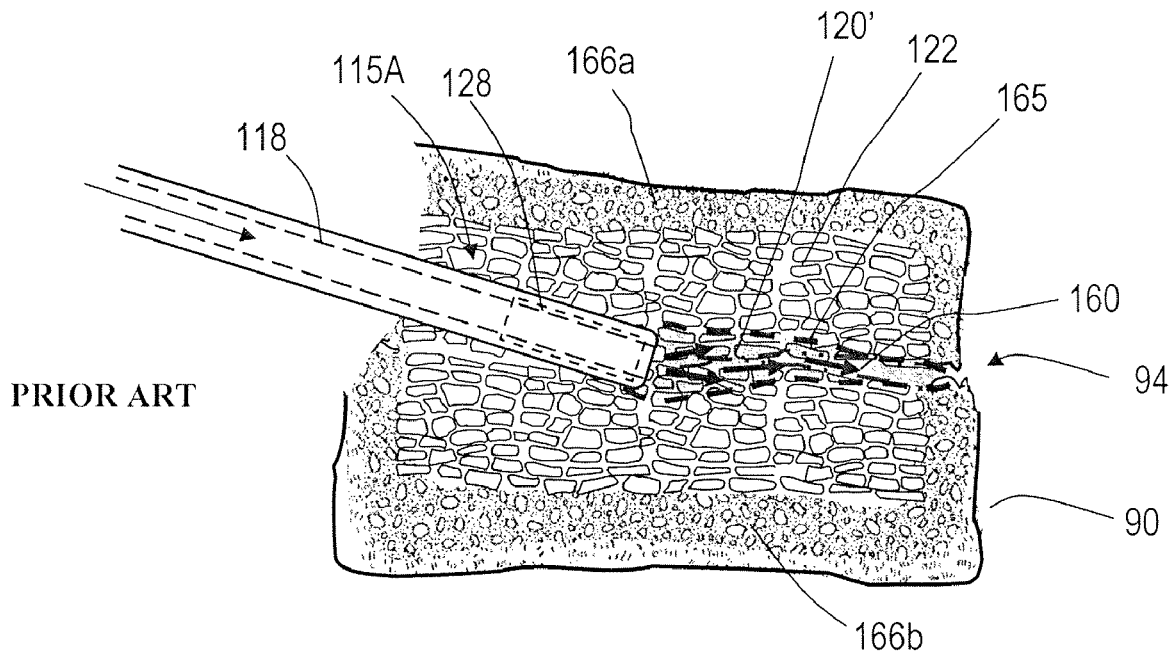
FIG. 5A is a schematic side view of a probe inserted into a vertebral body and injecting flowable fill material into the vertebral body.
Figure 5B:
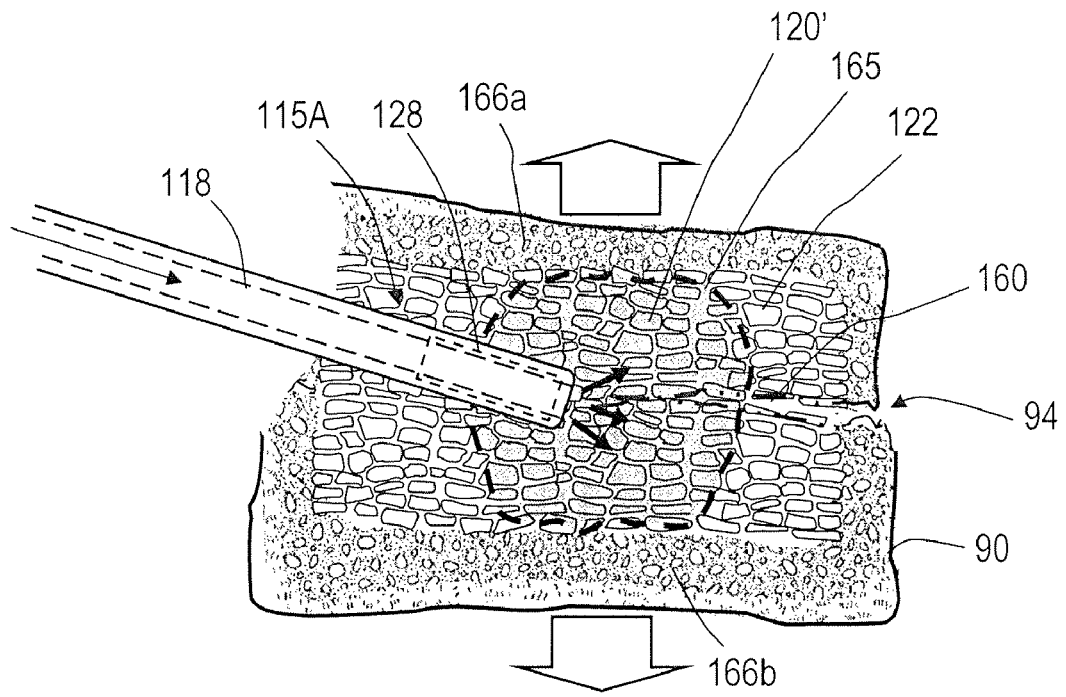
FIG. 5B is a schematic side view of the probe in FIG. 5A injecting a relatively high viscosity volume of flowable fill material into the vertebral body, in accordance with one embodiment of the present invention.

FIGS. 5A and 5B are views of a vertebra 90 that are useful for explaining relevant aspects of one embodiment of the invention wherein working end 110A is advanced into the region of fracture 94 in cancellous bone 122. FIG. 5A indicates system 100 being used to inject flow material 120 into the vertebra with the flow material having a viscosity similar to conventional vertebroplasty or kyphoplasty, for example having the consistency of toothpaste. FIG. 5A depicts the situation wherein high pressure injection of a low viscosity material can simply follow paths of least resistance along a recent fracture plane 160 to migrate anteriorly in an uncontrolled manner. The migration of fill material could be any direction, including posteriorly toward the spinal canal or into the disc space depending on the nature of the fracture.

FIG. 5B illustrates system 100 including actuation of Rf source 125A by controller 125B to contemporaneously heat the fill material to eject altered fill material 120' with a selected higher viscosity into cancellous bone 122, such as the viscosities described above. With a selected higher viscosity, FIG. 5B depicts the ability of the system to prevent extravasation of fill material and to controllably permeate and interdigitate with cancellous bone 122, rather than displacing cancellous bone, with a plume 165 that engages cortical bone vertebral endplates 166a and 166b. The fill material broadly engages surfaces of the cortical endplates to distribute pressures over the endplates. In a preferred embodiment, the fill material controllably permeates cancellous bone 122 and is ejected at a viscosity adequate to interdigitate with the cancellous bone 122. Fill material with a viscosity in the range of about 100,000 cps to 2,000,000 cps may be ejected, though even lower or higher viscosities may also be sufficient. The Rf source may selectively increase the viscosity of the fill material by about 10% or more as it is ejected from the introducer 115A. In other embodiments, the viscosity may be increased by about 20%, 50%, 100%, 500% or 1000% or more.

Still referring to FIG. 5B, it can be understood that continued inflows of high viscosity fill material 120' and the resultant expansion of plume 165 will apply forces on endplates 166a and 166b to at least partially restore vertebral height. It should be appreciated that the working end 115A can be translated axially between about the anterior third of the vertebral body and the posterior third of the vertebral body during the injection of fill material 120', as well as rotating the working end 115A which can be any of the types described above (FIGS. 3A-3C).

Figure 6:
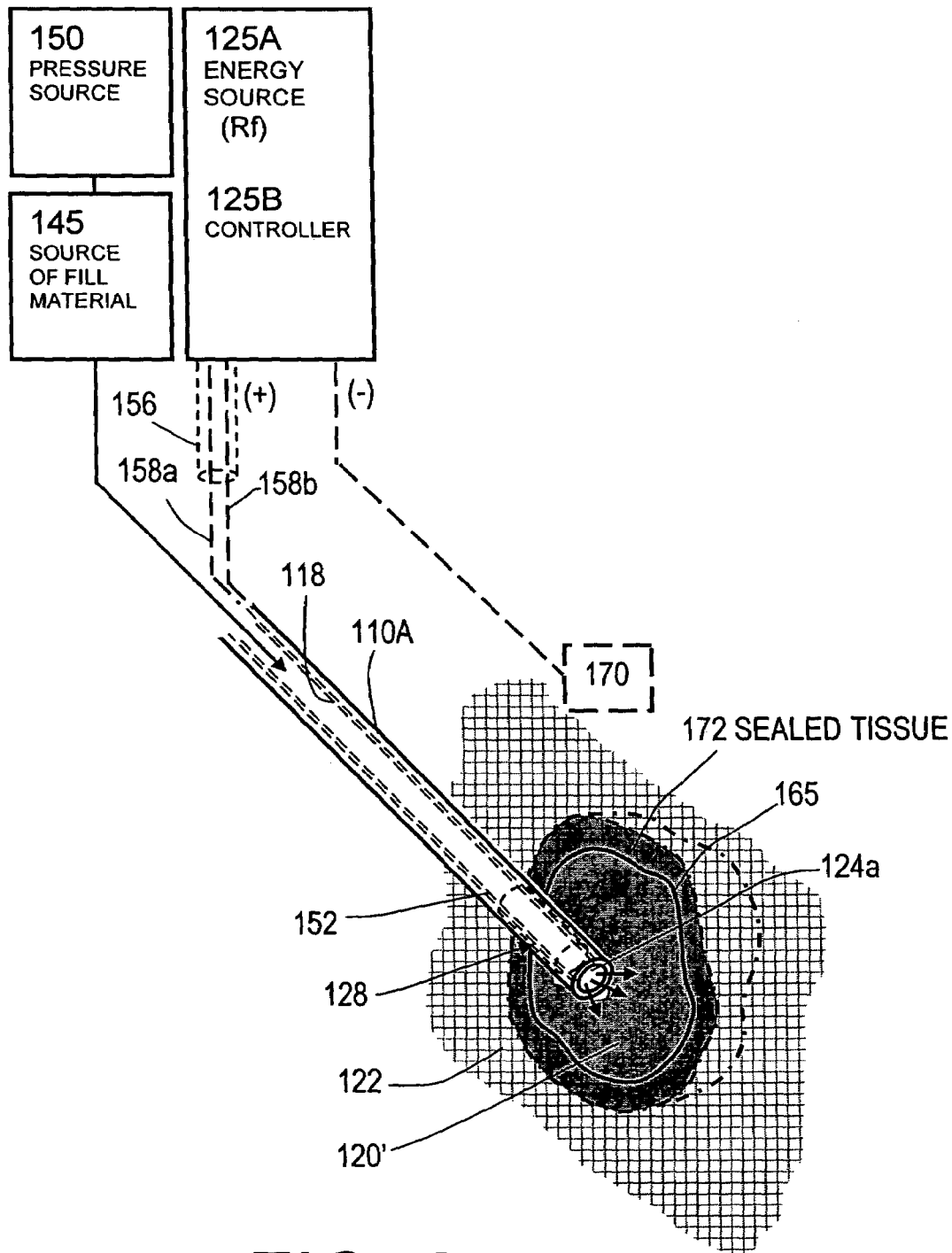
FIG. 6 is a schematic perspective view of a system for treating bone, in accordance with another embodiment.

FIG. 6 is a schematic view of an alternative embodiment of system 100 wherein Rf source 125A and controller 125B are configured to multiplex energy delivery to provide additional functionality. In one mode of operation, the system functions as described above and depicted in FIGS. 4 and 5B to alter flow properties of flowable fill material 120' as it is ejected from working end 115A. As can be seen in FIG. 6, the system further includes a return electrode or ground pad indicated at 170. Thus the system can be operated in a second mode of operation wherein electrodes 132a and 132b are switched to a common polarity (or the distal portion of sleeve 123 can comprise such an electrode) to function in a mono-polar manner in conjunction with ground pad 170. This second mode of operation advantageously creates high energy densities about the surface of plume 165 to thereby ohmically heat tissue at the interface of the plume 165 and the body structure.

In FIG. 6, the ohmically heated tissue is indicated at 172, wherein the tissue effect is coagulation of blood vessels, shrinkage of collagenous tissue and generally the sealing and ablation of bone marrow, vasculature and fat within the cancellous bone. The Rf energy levels can be set at a sufficiently high level to coagulate, seal or ablate tissue, with the controller delivering power based, for example, on impedance feedback which will vary with the surface area of plume 165. Of particular interest, the surface of plume 165 is used as an electrode with an expanding wavefront within cancellous bone 122. Thus, the vasculature within the vertebral body can be sealed by controlled ohmic heating at the same time that fill material 120' is permeating the cancellous bone. Within the vertebral body are the basivertebral (intravertebral) veins which are paired valveless veins connecting with numerous venous channels within the vertebra (pars spongiosa/red bone marrow). These basivertebral veins drain directly into the external vertebral venous plexus (EVVP) and the superior and inferior vena cava. The sealing of vasculature and the basivertebral veins is particularly important since bone cement and monomer embolism has been frequently observed in vertebroplasty and kyphoplasty cases (see "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004). It can be thus understood that the method of using the system 100 creates and expands a "wavefront" of coagulum that expands as the plume 165 of fill material expands. The expandable coagulum layer 172, besides sealing the tissue from emboli, contains and distributes pressures of the volume of infill material 120' about the plume surface.

The method depicted in FIG. 6 provides an effective means for sealing tissue via ohmic (Joule) heating. It has been found that passive heat transfer from the exothermic reaction of a bone cement does not adequately heat tissue to the needed depth or temperature to seal intravertebral vasculature. In use, the mode of operation of the system 100 in a mono-polar manner for ohmically heating and sealing tissue can be performed in selected intervals alone or in combination with the bi-polar mode of operation for controlling the viscosity of the injected fill material.

In general, one aspect of the vertebroplasty or osteoplasty method in accordance with one of the embodiments disclosed herein allows for in-situ control of flows of a flowable fill material, and more particularly comprises introducing a working end of an introducer sleeve into cancellous bone, ejecting a volume of flowable fill material having a selected viscosity and contemporaneously applying energy (e.g., Rf energy) to the fill material from an external source to thereby increase the viscosity of at least portion of the volume to prevent fill extravasation. In a preferred embodiment, the system increases the viscosity by about 20% or more. In another preferred embodiment, the system increases the viscosity by about 50% or more.

In another aspect of one embodiment of a vertebroplasty method, the system 100 provides means for ohmically heating a body structure about the surface of the expanding plume 165 of fill material to effectively seal intravertebral vasculature to prevent emboli from entering the venous system. The method further provides an expandable layer of coagulum about the infill material to contain inflow pressures and distribute further expansion forces over the vertebral endplates.

In a preferred embodiment, the coagulum expands together with at least a portion of the infill material to engage and apply forces to endplates of the vertebra.

Of particular interest, one embodiment of fill material 120 as used in the systems described herein (see FIGS. 2A, 4, 5A-5B and 6) is a composite comprising an in-situ hardenable or polymerizable cement component 174 and an electrically conductive filler component 175 in a sufficient volume to enable the composite to function as a dispersable electrode (FIG. 6). In one type of composite, the conductive filler component is any biocompatible conductive metal. In another type of composite, the conductive filler component is a form of carbon. The biocompatible metal can include at least one of titanium, tantalum, stainless steel, silver, gold, platinum, nickel, tin, nickel titanium alloy, palladium, magnesium, iron, molybdenum, tungsten, zirconium, zinc, cobalt or chromium and alloys thereof. The conductive filler component has the form of at least one of filaments, particles, microspheres, spheres, powders, grains, flakes, granules, crystals, rods, tubules and the like. Such conductive filler components can be at least one of solid, porous or hollow, with conductive filaments 176a illustrated in FIG. 7A and conductive particles 176b depicted in FIG. 7B.

Figure 7A:
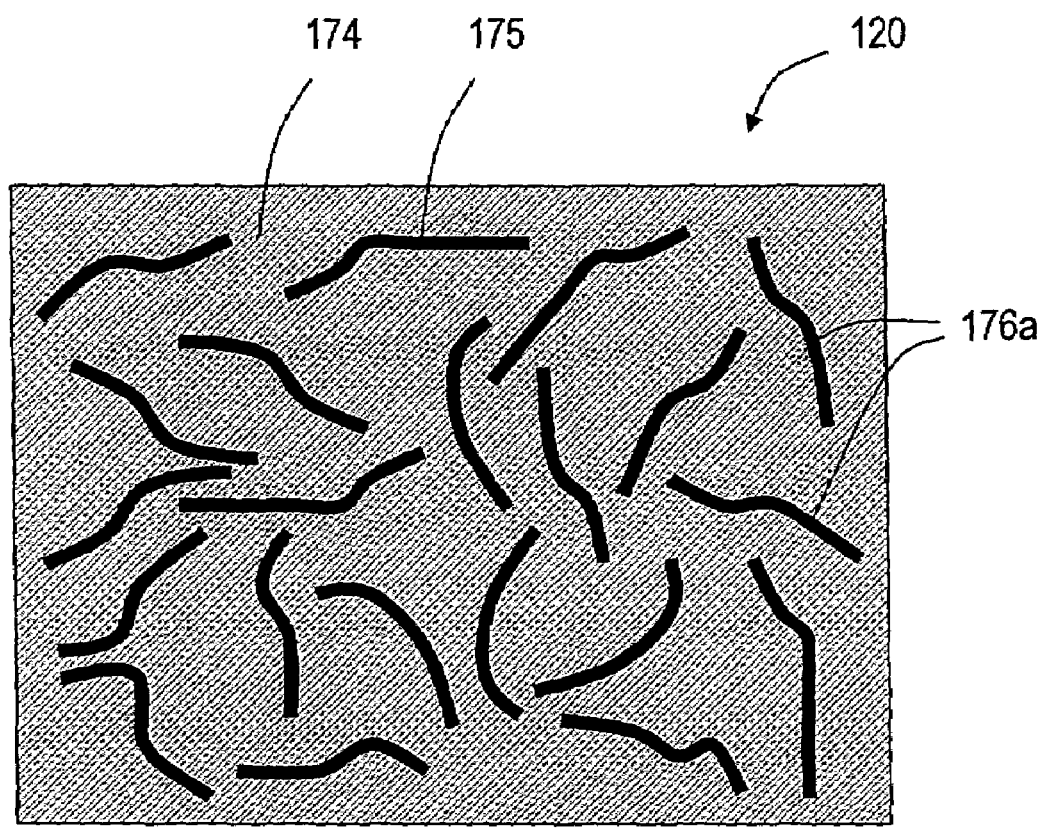
FIG. 7A is a schematic sectional view of a fill material, in accordance with one embodiment.
Figure 7B:
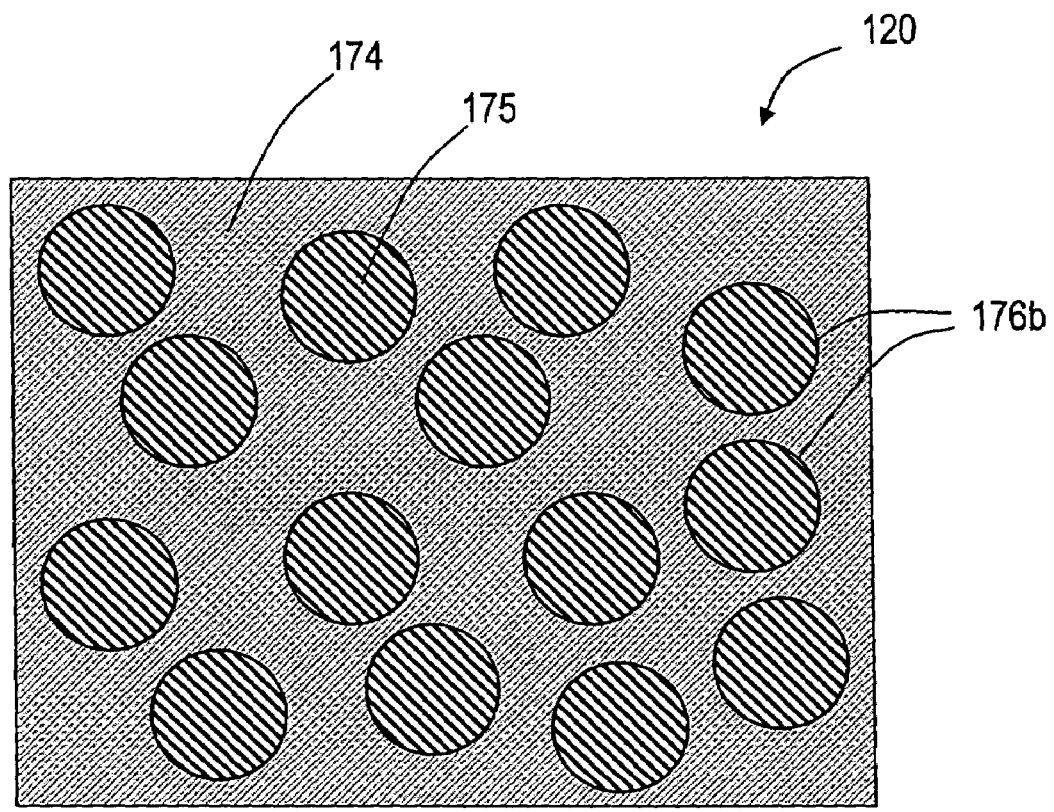
FIG. 7B is a schematic sectional view of a fill material, in accordance with another embodiment.

In a preferred embodiment, the conductive filler comprises chopped microfilaments or ribbons of a metal as in FIG. 7A that have a cross-section dimension across a major axis ranging between about 0.0005" and 0.01". The lengths of the microfilaments or ribbons range from about 0.01" to 0.50". The microfilaments or ribbons are of stainless steel or titanium and are optionally coated with a thin gold layer or silver layer that can be deposited by electroless plating methods. Of particular interest, the fill material 120 of FIG. 7A has an in situ hardenable cement component 174 than has a first low viscosity and the addition of the elongated microfilament conductive filler component 175 causes the composite 120 to have a substantially high apparent viscosity due to the high surface area of the microfilaments and its interaction with the cement component 174.

In another embodiment of bone fill material 120, the conductive filler component comprises elements that have a non-conductive core portion with a conductive cladding portion for providing electrosurgical functionality. The non-conductive core portions are selected from the group consisting of glass, ceramic or polymer materials. The cladding can be any suitable conductive metal as described above that can be deposited by electroless plating methods.

In any embodiment of bone fill material that uses particles, microspheres, spheres, powders, grains, flakes, granules, crystals or the like, such elements can have a mean dimension across a principal axis ranging from about 0.5 micron to 2000 microns. More preferably, the mean dimension across a principal axis range from about 50 microns to 1000 microns. It has been found that metal microspheres having a diameter of about 800 microns are useful for creating conductive bone cement that can function as an electrode.

In one embodiment, a conductive filler comprising elongated microfilaments wherein the fill material has from about 0.5% to 20% microfilaments by weight. More preferably, the filaments are from about 1.0% to 10% by weight of the fill material. In other embodiments wherein the conductive filler comprises particles or spheres, the conductive filler can comprise from about 5% of the total weight to about 80% of the weight of the material.

In an exemplary fill material 120, the hardenable component can be any in-situ hardenable composition such as at least one of PMMA, monocalcium phosphate, tricalcium phosphate, calcium carbonate, calcium sulfate or hydroxyapatite.

Figure 8A:
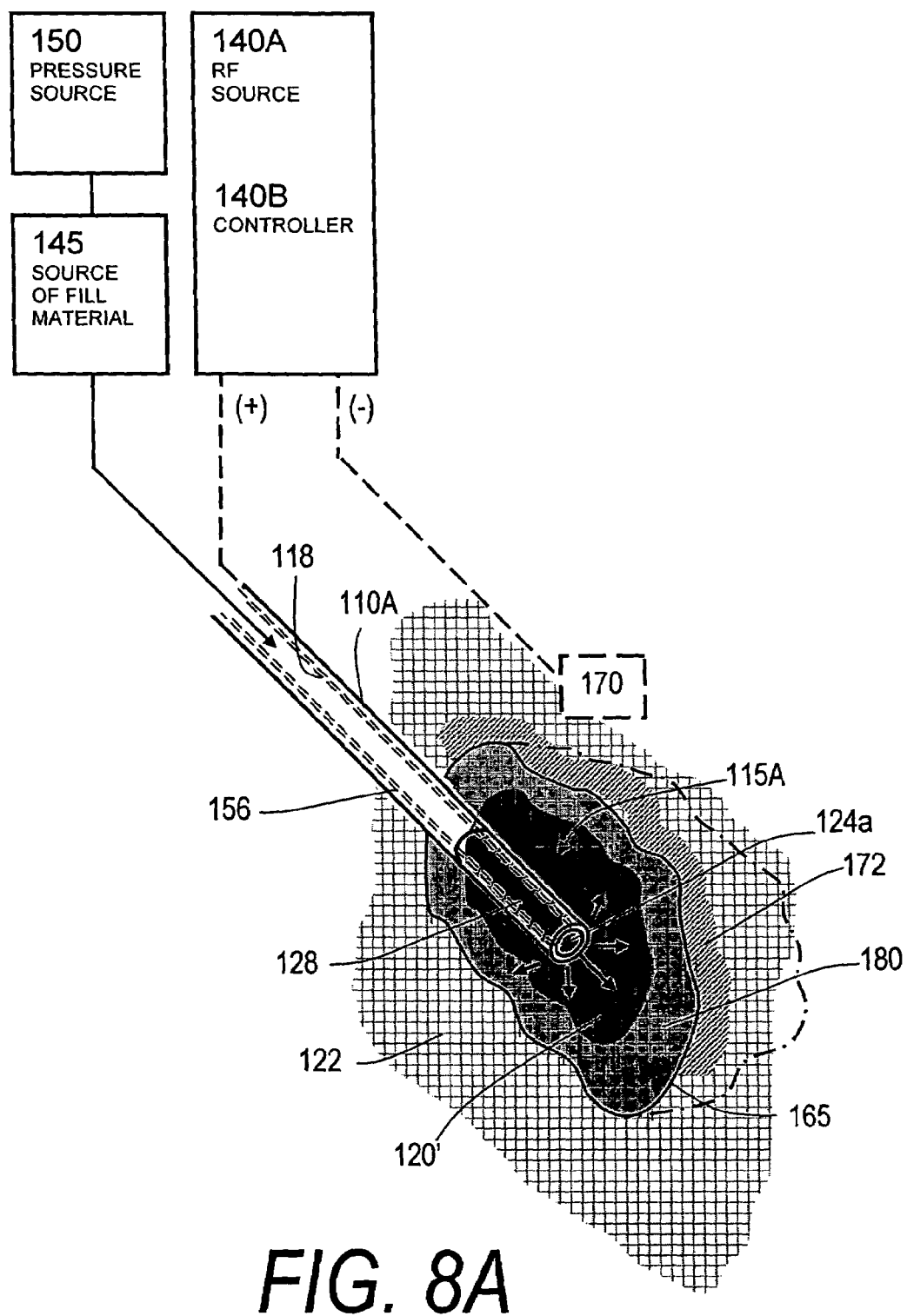
FIG. 8A is a schematic perspective view of a system for treating bone, in accordance with another embodiment.
Figure 8B:
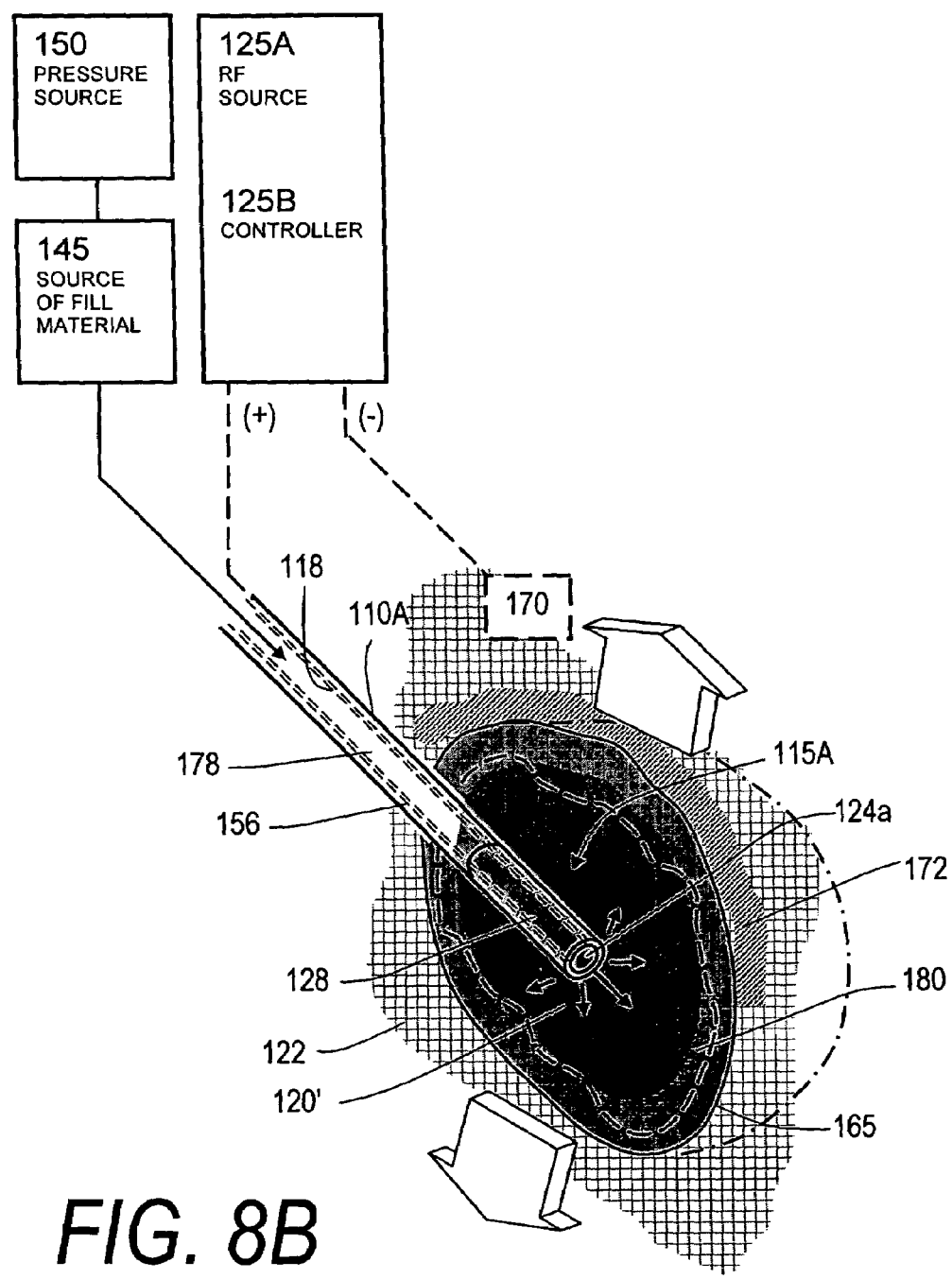
FIG. 8B is a schematic perspective view of the system in FIG. 8A, injecting an additional volume of fill material into a vertebral body.

Referring now to FIGS. 8A and 8B, an alternative method is shown wherein the system 100 and method are configured for creating asymmetries in properties of the infill material and thereby in the application of forces in a vertebroplasty. In FIG. 8A, the pressure mechanism 150 is actuated to cause injection of an initial volume or aliquot of fill material 120' that typically is altered in viscosity in working end 110A as described above—but the method encompasses flows of fill material having any suitable viscosity. The fill material is depicted in FIGS. 8A and 8B as being delivered in a unilateral transpedicular approach, but any extrapedicular posterior approach is possible as well as any bilateral posterior approach. The system in FIGS. 8A-8B again illustrates a vertical plane through the fill material 120' that flows under pressure into cancellous bone 122 with expanding plume or periphery indicated at 165. The plume 165 has a three dimensional configuration as can be seen in FIG. 8B, wherein the pressurized flow may first tend to flow more horizontally that vertically. One embodiment of the method of the invention includes the physician translating the working end slightly and/or rotating the working end so that flow outlets 124a are provided in a selected radial orientation. In a preferred embodiment, the physician intermittently monitors the flows under fluoroscopic imaging as described above.

FIG. 8B depicts a contemporaneous or subsequent energy-delivery step of the method wherein the physician actuates Rf electrical source 125A and controller 125B to cause Rf current delivery from at least one electrode emitter 128 to cause ohmic (Joule) heating of tissue as well as internal heating of the inflowing fill material 120'. In this embodiment, the exterior surface of sleeve 123 is indicated as electrode or emitter 128 with the proximal portion of introducer 110A having an insulator coating 178. The Rf energy is preferably applied in an amount and for a duration that coagulates tissue as well as alters a flowability property of surface portions 180 of the initial volume of fill material proximate the highest energy densities in tissue.

In one preferred embodiment, the fill material 120 is particularly designed to create a gradient in the distribution of conductive filler with an increase in volume of material injected under high pressure into cancellous bone 122. This aspect of the method in turn can be used advantageously to create asymmetric internal heating of the fill volume. In this embodiment, the fill material 120 includes a conductive filler of elongated conductive microfilaments 176a (FIG. 7A). The filaments are from about 2.0% to 5% by weight of the fill material, with the filaments having a diameter ranging between 0.001" and 0.010" and a length ranging from 1.0 mm to 5.0 mm. It has been found that elongated conductive microfilaments 176a result in resistance to flows thereabout which causes such microfilaments to aggregate away from the most active media flows that are concentrated in the center of the vertebra proximate to outlet 124a. Thus, the conductive microfilaments 176a attain a higher concentration in the peripheral or surface portion 180 of the plume which in turn will result in greater internal heating of the fill portions having such higher concentrations of conductive filaments. The active flows also are controlled by rotation of introducer 110A to eject the material preferentially, for example laterally as depicted in FIG. 8A and 8B rather that vertically. The handle 106 of the probe 105 preferably has markings to indicate the rotational orientation of the outlets 124b.

FIG. 8A depicts the application of Rf energy in a monopolar manner between electrode emitter 128 and ground pad 170, which thus causes asymmetric heating wherein surface portion 180 heating results in greater polymerization therein. As can be seen in FIG. 8A, the volume of fill material thus exhibits a gradient in a flowability property, for example with surface region 180 having a higher viscosity than inflowing material 120' as it is ejected from outlet 124a. In one embodiment, the gradient is continuous. Such heating at the plume periphery 165 can create an altered, highly viscous surface region 180. This step of the method can transform the fill material to have a gradient in flowability in an interval of about 5 seconds to 500 seconds with surface portion 180 being either a highly viscous, flowable layer or an elastomer that is expandable. In preferred embodiments, the interval of energy delivery required less than about 120 seconds to alter fill material to a selected asymmetric condition. In another aspect of the invention, the Rf energy application for creating the gradient in flowability also can be optimized for coagulating and sealing adjacent tissue.

The combination of the viscous surface portion 180 and the tissue coagulum 172 may function as an in-situ created stretchable, but substantially flow-impervious, layer to contain subsequent high pressure inflows of fill material. Thus, the next step of the method of the invention is depicted in FIG. 8B which includes injecting additional fill material 120' under high pressure into the interior of the initial volume of fill material 120 that then has a highly viscous, expandable surface. The viscous, expandable surface desirably surrounds cancellous bone. By this means, the subsequent injection of fill material can expand the fill volume to apply retraction forces on the vertebra endplates 166a and 166b to provide vertical jacking forces, distracting cortical bone, for restoring vertebral height, as indicated by the arrows in FIG. 8B. The system can generate forces capable of breaking callus in cortical bone about a vertebral compression fracture when the fracture is less than completely healed.

In one embodiment, the method includes applying Rf energy to create highly viscous regions in a volume of fill material and thereafter injecting additional fill material 120 to controllably expand the fill volume and control the direction of force application. The scope of the method further includes applying Rf energy in multiple intervals or contemporaneous with a continuous flow of fill material. The scope of the method also includes applying Rf in conjunction with imaging means to prevent unwanted flows of the fill material. The scope of the invention also includes applying Rf energy to polymerize and accelerate hardening of the entire fill volume after the desired amount of fill material has been injected into a bone.

Figure 9A:
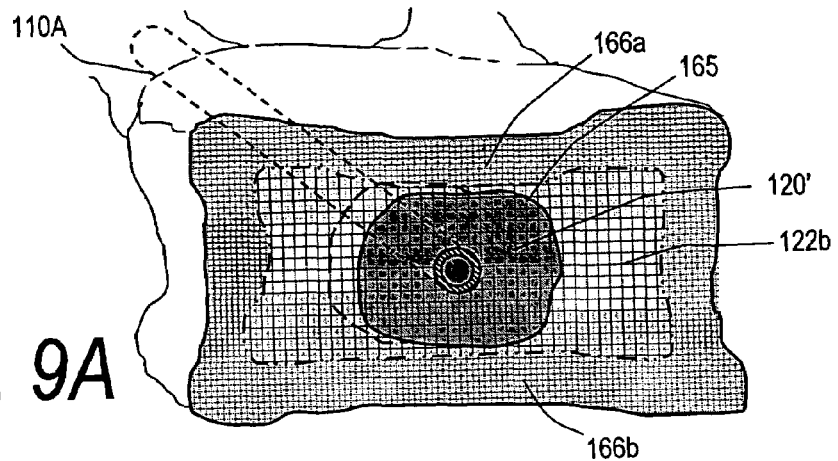
FIG. 9A is a schematic sectional view of one step in a method for treating bone, in accordance with one embodiment.
Figure 9B:
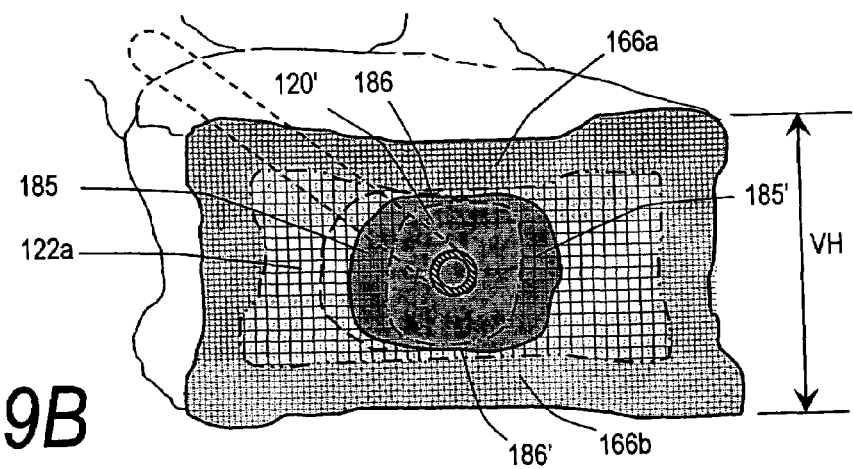
FIG. 9B is a schematic sectional view of another step in a method for treating bone, in accordance with one embodiment.
Figure 9C:
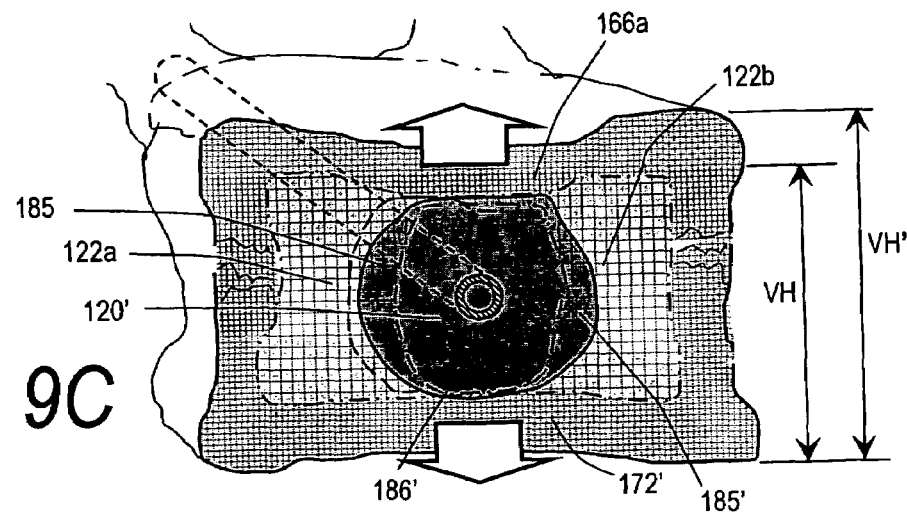
FIG. 9C is a schematic sectional view of still another step in a method for treating bone, in accordance with one embodiment.

In another embodiment, the method includes creating Rf current densities in selected portions of the volume of fill material 120 to create asymmetric fill properties based on particular characteristics of the vertebral body. For example, the impedance variances in cancellous bone and cortical bone can be used to create varied Rf energy densities in fill material 120 to create asymmetric properties therein. Continued injection of fill material 120 are thus induced to apply asymmetric retraction forces against cortical endplates 166a and 166b, wherein the flow direction is toward movement or deformation of the lower viscosity portions and away from the higher viscosity portions. In FIGS. 9A-9C, it can be seen that in a vertebroplasty, the application of Rf energy in a mono-polar manner as in FIG. 6 naturally and preferentially creates more highly viscous, deeper "altered" properties in surfaces of the lateral peripheral fill volumes indicated at 185 and 185' and less viscous, thinner altered surfaces in the superior and inferior regions 186 and 186' of fill material 120. This effect occurs since Rf current density is localized about paths of least resistance which are predominantly in locations proximate to highly conductive cancellous bone 122a and 122b. The Rf current density is less in locations proximate to less conductive cortical bone indicated at 166a and 166b. Thus, it can be seen in FIG. 9B that the lateral peripheral portions 185 and 185' of the first flows of fill material 120 are more viscous and resistant to flow and expansion than the thinner superior and inferior regions. In FIG. 9C, the asymmetrical properties of the initial flows of fill material 120 allows the continued flows to apply retraction forces in substantially vertical directions to reduce the vertebral fracture and increase vertebral height, for example from VH (FIG. 9B) to VH' in FIG. 9C.

Figure 10A:
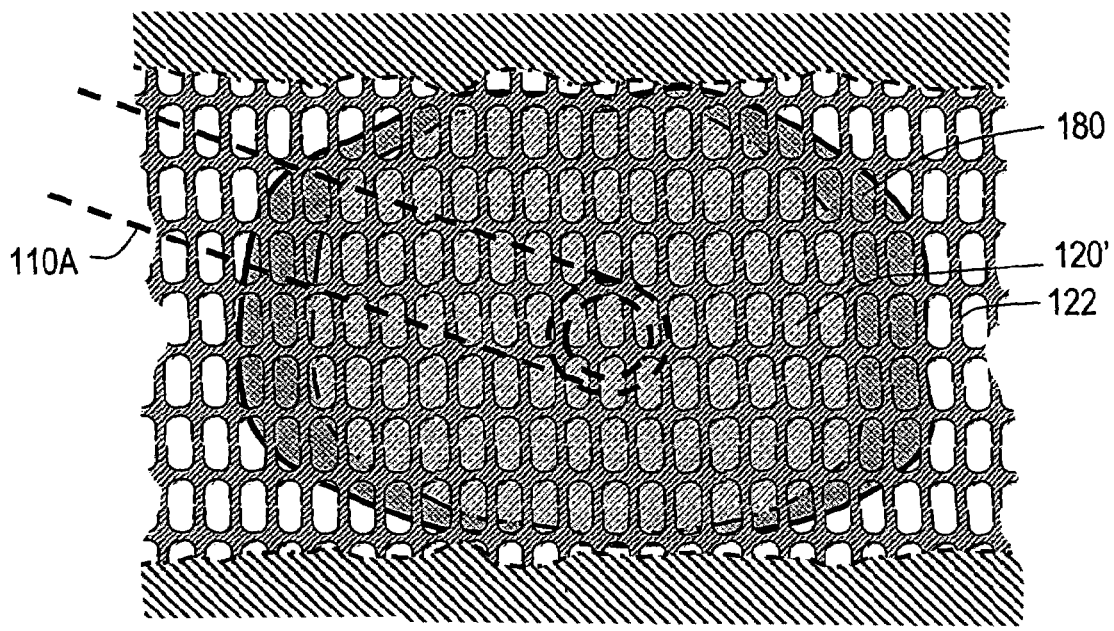
FIG. 10A is a schematic sectional view of a step in a method for treating bone, in accordance with another embodiment.
Figure 10B:
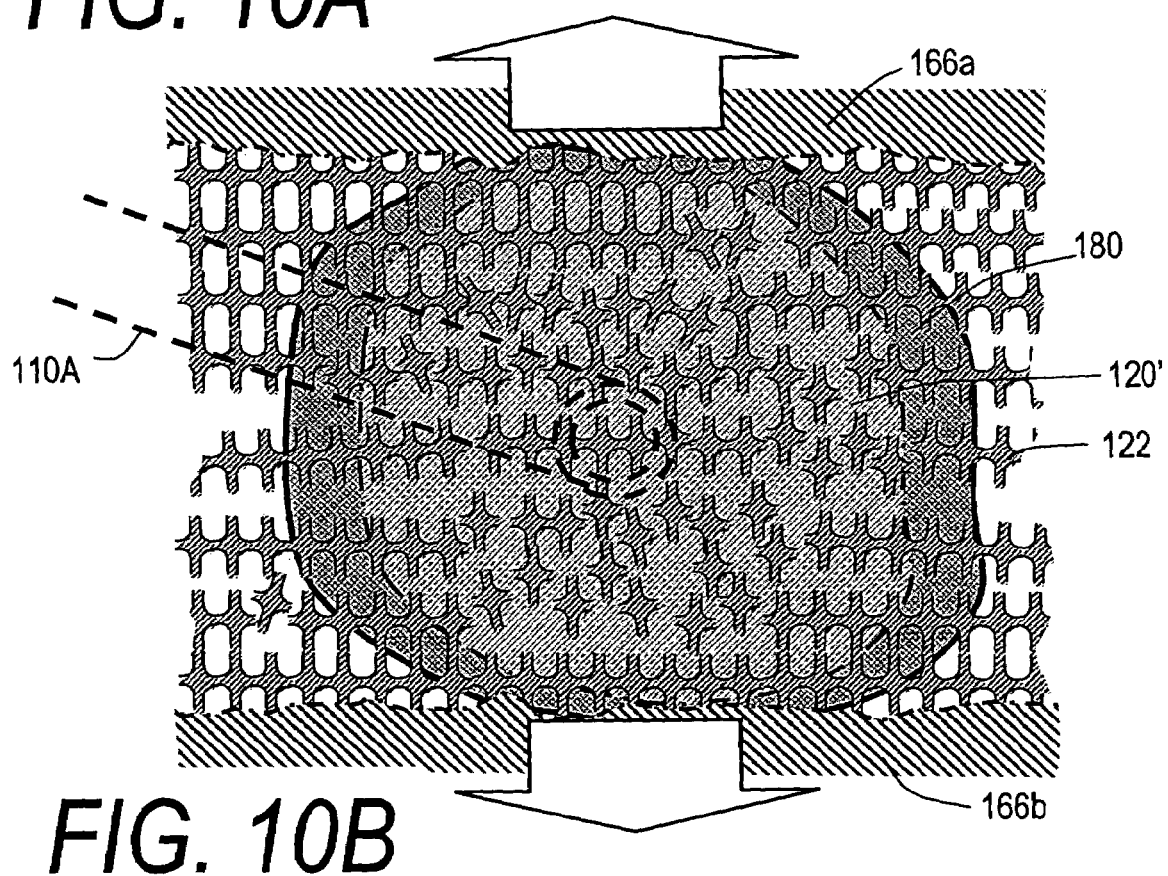
FIG. 10B is a schematic sectional view of another step in a method for treating bone, in accordance with another embodiment.

FIGS. 10A and 10B are schematic views that further depict a method corresponding to FIGS. 9B and 9C that comprises expanding cancellous bone for applying retraction forces against cortical bone, e.g., endplates of a vertebra in a vertebroplasty. As can be seen in FIG. 10A, an initial volume of flowable fill material 120 is injected into cancellous bone wherein surface region 180 is altered as described above to be highly viscous or to comprise and elastomer that is substantially impermeable to interior flows but still be expandable. The surface region 180 surrounds subsequent flows of fill material 120' which interdigitate with cancellous bone. Thereafter, as shown in FIG. 10B, continued high pressure inflow into the interior of the fill material thereby expands the cancellous bone 122 together with the interdigitated fill material 120'. As can be seen in FIG. 10B, the expansion of cancellous bone 122 and fill material 120' thus applies retraction forces to move cortical bone endplates 166a and 166b. The method of expanding cancellous bone can be used to reduce a bone fracture such as a vertebral compression fracture and can augment or restore the height of a fractured vertebra. The system thus can be used to support retract and support cortical bone, and cancellous bone. The method can also restore the shape of an abnormal vertebra, such as one damaged by a tumor.

After utilizing system 100 to introduce, alter and optionally harden fill material 120 as depicted in FIGS. 9A-9C and 10A-10B, the introducer 110A can be withdrawn from the bone. Alternatively, the introducer 110A can have a release or detachment structure indicated at 190 for de-mating the working end from the proximal introducer portion as described in co-pending U.S. patent application Ser. No.11/130,843, filed May 16, 2005, the entirety of which is hereby incorporated by reference.

Figure 11A:
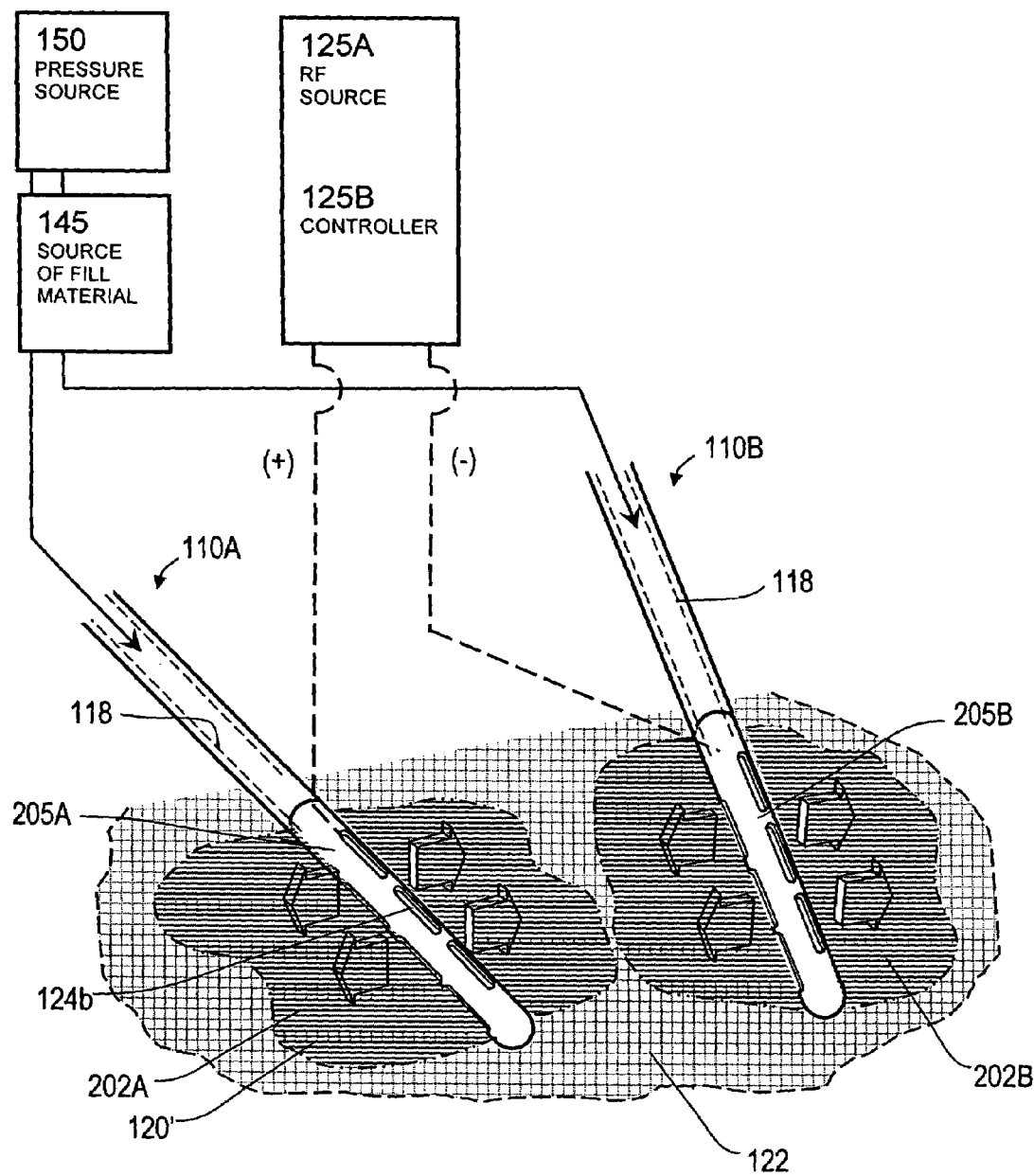
FIG. 11A is a schematic perspective view of a system for treating bone, in accordance with another embodiment.
Figure 11B:
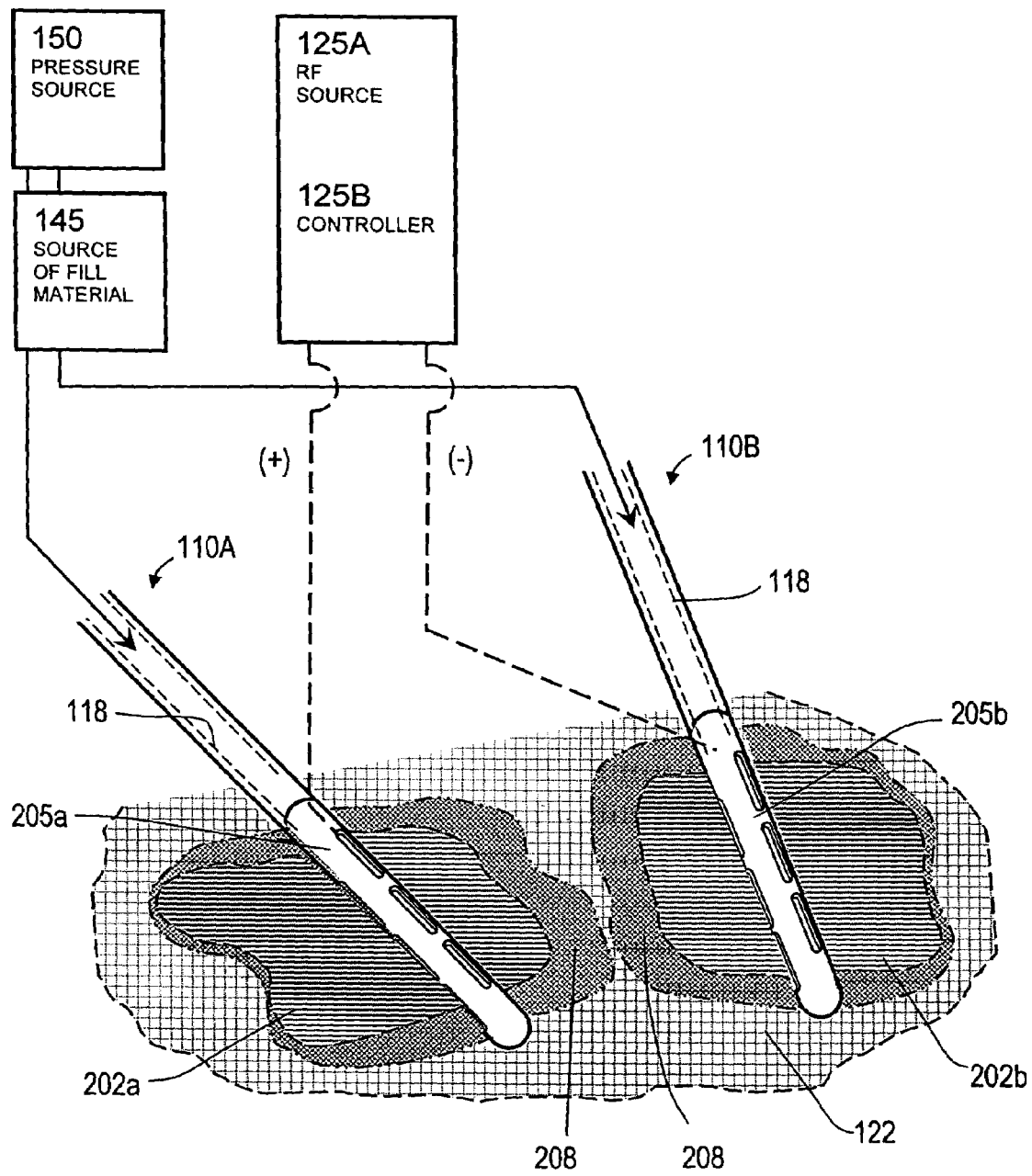
FIG. 11B is a schematic perspective view of the system in FIG. 11A, applying energy to a fill material.

Another system embodiment 200 for controlling flow directions and for creating asymmetric properties is shown in FIGS. 11A and 11B, wherein first and second introducers 110A and 110B similar to those described above are used to introduce first and second independent volumes 202a and 202b of fill material 120 in a bilateral approach. In this embodiment, the two fill volumes function as opposing polarity electrodes in contact with electrodes 205a and 205b of the working ends. Current flow between the electrodes thus operates in a bi-polar manner with the positive and negative polarities indicated by the (+) and (−) symbols. In this method, it also can be seen that the highest current density occurs in the three dimensional surfaces of volumes 202a and 202b that face one another. This results in creating the thickest, high viscosity surfaces 208 in the medial, anterior and posterior regions and the least "altered" surfaces in the laterally outward regions. This method is well suited for preventing posterior and anterior flows and directing retraction forces superiorly and inferiorly since lateral flow are contained by the cortical bone at lateral aspects of the vertebra. The system can further be adapted to switch ohmic heating effects between the bi-polar manner and the mono-polar manner described previously.

Figure 12:
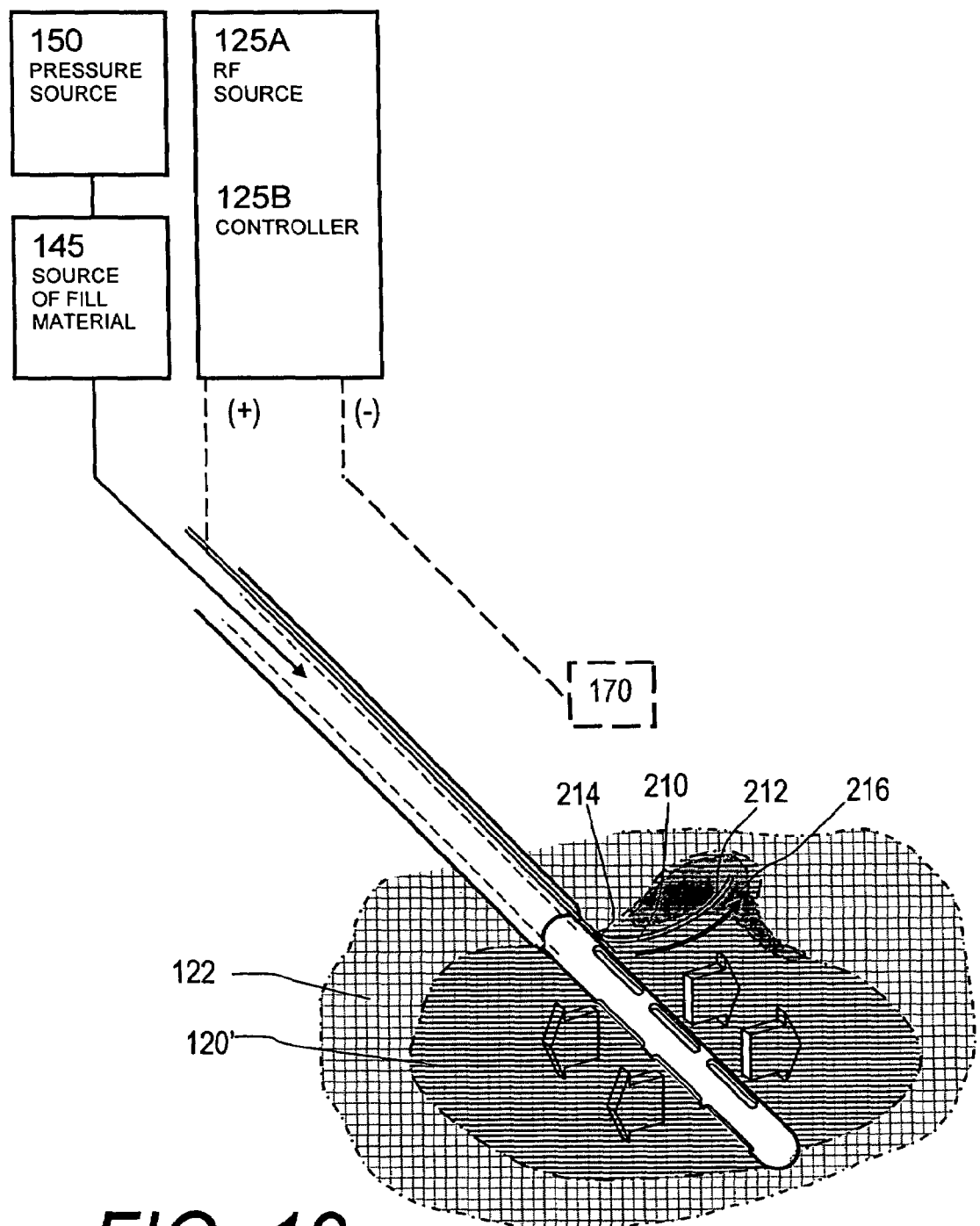
FIG. 12 is a schematic perspective view of a system for treating bone, in accordance with another embodiment.

Now referring to FIG. 12, another embodiment is shown wherein a translatable member 210 that functions as an electrode is carried by introducer 110A. In a preferred embodiment, the member 210 is a superelastic nickel titanium shape memory wire that has a curved memory shape. The member 210 can have a bare electrode tip 212 with a radiopaque marking and is otherwise covered by a thin insulator coating. In FIG. 12, it can be seen that the introducer can be rotated and the member can be advanced from a port 214 in the working end 115A under imaging. By moving the electrode tip 212 to a desired location and then actuating RF current, it is possible to create a local viscous or hardened region 216 of fill material 120. For example, if imaging indicates that fill material 120 is flowing in an undesired direction, then injection can be stopped and Rf energy can be applied to harden the selected location.

In another embodiment similar to the one shown in FIG. 12, the translatable member 210 can comprise a hollow needle that injects a chemical agent (e.g., a catalyst) to accelerate local curing of the fill material 120. Alternatively, the hollow needle can deliver a microencapsulated chemical agent that is released by Rf energy delivery to sacrifice the microcapsule.

Figure 13A:
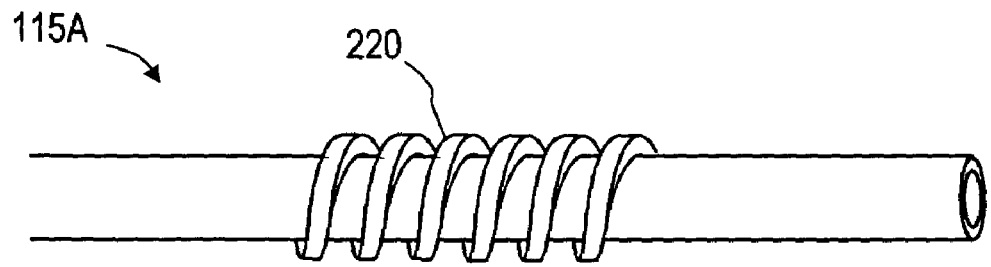
FIG. 13A is a side view of a working end of an introducer, in accordance with one embodiment.
Figure 13B:
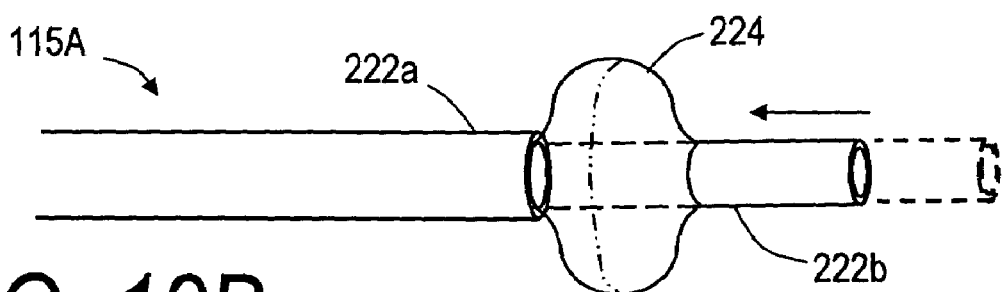
FIG. 13B is a side view of a working end of an introducer, in accordance with another embodiment.
Figure 13C:
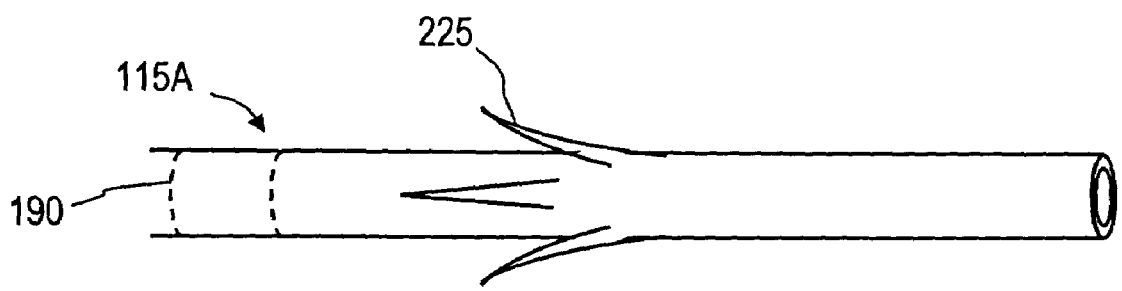
FIG. 13C is a side view of a working end of an introducer, in accordance with yet another embodiment.
Figure 13D:
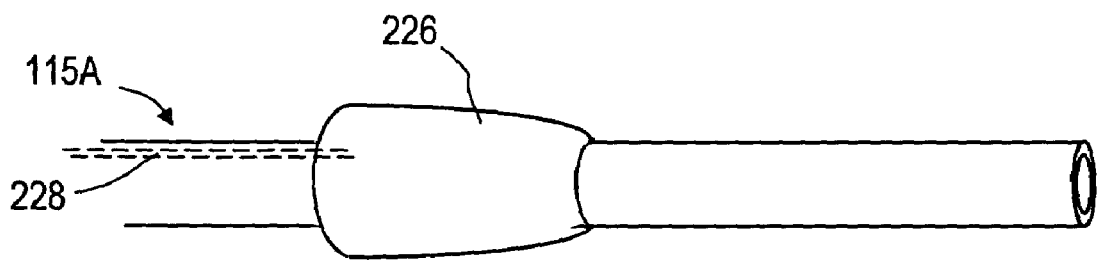
FIG. 13D is a side view of a working end of an introducer, in accordance with still another embodiment.

FIGS. 13A-13D illustrate other embodiments of the introducer 110A, which include structures for engaging the working end 115A in bone to substantially prevent it from moving proximally when very high pressures are used to inject bone fill material 120, for example to augment vertebral height when treating a VCF. FIG. 13A illustrates a working end with threads 220 for helically advancing the introducer which will secure the introducer in bone. FIG. 13B illustrates a working end with first and second concentric sleeves 222a and 222b that can be used to buckle and radially expand a resilient element 224 such as a rubber member. Alternatively, the system of FIG. 13B could be configured to buckle at least one metal element. FIG. 13C illustrates a working end with barbs 225 that engage the bone as the structure is moved proximally. In the illustrated embodiment, such a working end can be detached using a detachment mechanism indicated at 190 as described above. In another embodiment, the introducer barbs 225 can be configured to collapse somewhat under rotation to thereby rotate and withdraw the introducer from bone. FIG. 13D illustrates a working end with an expandable balloon structure 226 for gripping bone that is inflated through lumen 228 from an inflation source.

Figure 14:
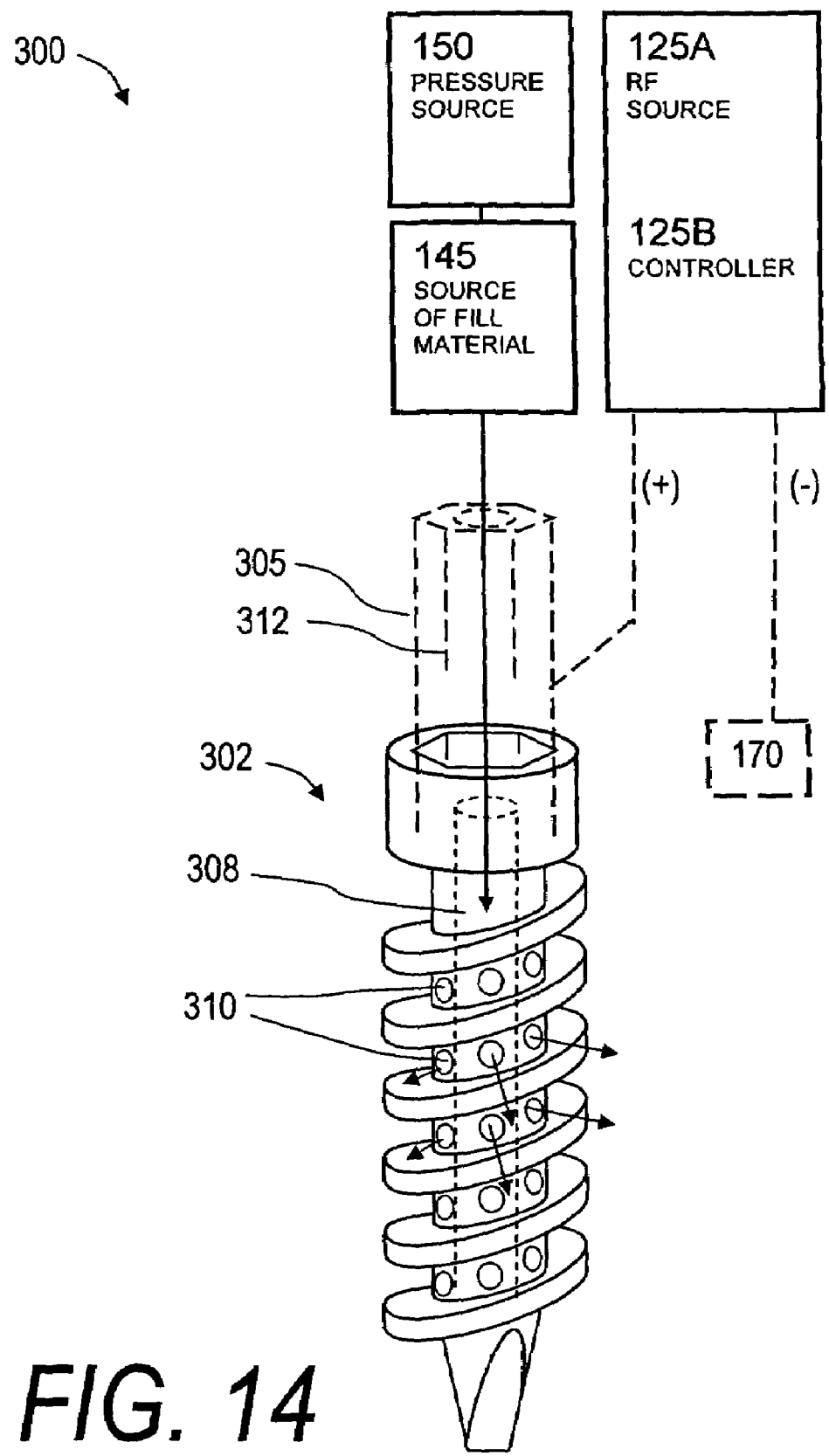
FIG. 14 is a perspective view of a system for treating bone, in accordance with another embodiment.

FIG. 14 illustrates another embodiment of the invention wherein the on-demand hardenable fill material 120 is combined with an implant 300 such as a bone screw, pin, shaft, joint reconstruction body or the like. As one example of an implant, FIG. 14 illustrates a metal bone screw 302 that cooperates with driver member 305 for helically driving the screw. The bone screw 302 has a lumen 308 that communicates with a plurality of outlets 310 in the implant body. In one embodiment, the driver 305 has a cooperating bore 312 that is coupled to a source 145 of conductive fill material 120 as described above. Further, the system includes Rf source 125A and controller 125B for applying Rf energy to harden the fill material on demand. In one embodiment, the Rf source is coupled to the electrically conductive driver 305 which carries Rf current to the bone screw by contact. As can be seen in FIG. 14, the method of the invention includes driving the bone screw in a bone, and then injecting the fill material 120 which will flow through outlets 310 (see arrows) in the implant. Thereafter, the Rf source is actuated to cure the fill material 120 to thereby fix the implant in bone.

It should be appreciated that the system FIG. 14 can be coupled with any type of bone implant, including joint reconstruction components for hips, knees, shoulders and the like, ligament or tendon implants that are fixed in a bore in bone, reconstructive surgery implants, and any other screw, pin or plate or the like.

The scope of the invention further extends to cure-on-demand fill material that can be used for disc nucleus implants, wherein the conductive fill material in injected to conform to the shape of a space wherein Rf current is then applied to increase the modulus of the material on demand to a desired level that is adapted for dynamic stabilization. Thus, the Rf conductive filler material 120 can be engineered to reach a desired modulus that is less than that of a hardened fill material used for bone support. In this embodiment, the fill material is used to support a disc or portion thereof. The cure-on-demand fill material also can be configured as an injectable material to repair or patch a disc annulus as when a tear or herniation occurs.

The scope of the invention further extends to cure-on-demand fill material that can be used for injection into a space between vertebrae for intervertebral fusion. The injection of fill material can conform to a space created between two adjacent vertebrae, or can be injected into notches or bores in two adjacent vertebrae and the intervening space, and then cured by application of Rf current to provide a substantially high modulus block to cause bone fusion.

In any embodiment such as for intervertebral fusion or for bone support in VCFs, the system can further include the injection of a gas (such as carbon dioxide) into the fill material before it is injected from a high pressure source. Thereafter, the gas can expand to form voids in the fill material as it is cured to create porosities in the hardened fill material for allowing rapid bone ingrowth into the fill material.

In a related method of the invention, the fill material 120 can be introduced into the cancellous bone 122 in different aliquots wherein each volume carries a different type of conductive filler, e.g., with different volume percentages of conductive filler or different dimensions of conductive fillers. In one embodiment, the secondary aliquots of fill material are not conductive.

In related methods of the invention, the system of the invention can use any suitable energy source, other that radiofrequency energy, to accomplish the purpose of altering the viscosity of the fill material 120. The method of altering fill material can be at least one of a radiofrequency source, a laser source, a microwave source, a magnetic source and an ultrasound source. Each of these energy sources can be configured to preferentially deliver energy to a cooperating, energy sensitive filler component carried by the fill material. For example, such filler can be suitable chomophores for cooperating with a light source, ferromagnetic materials for cooperating with magnetic inductive heating means, or fluids that thermally respond to microwave energy.

The scope of the invention includes using additional filler materials such as porous scaffold element and materials for allowing or accelerating bone ingrowth. In any embodiment, the filler material can comprise reticulated or porous elements of the types disclosed in co-pending U.S. patent application Ser. No. 11/146,891, filed Jun. 7, 2005, titled "Implants and Methods for Treating Bone" which is incorporated herein by reference in its entirety and should be considered a part of this specification. Such fillers also carry bioactive agents. Additional fillers, or the conductive filler, also can include thermally insulative solid or hollow microspheres of a glass or other material for reducing heat transfer to bone from the exothermic reaction in a typical bone cement component.

The above description of the invention is intended to be illustrative and not exhaustive. Particular characteristics, features, dimensions and the like that are presented in dependent claims can be combined and fall within the scope of the invention. The invention also encompasses embodiments as if dependent claims were alternatively written in a multiple dependent claim format with reference to other independent claims. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A method for treating bone, comprising:
providing a flowable infill material for infill of an interior region of a bone;
loading the infill material into an injector system having a portion positionable within the bone, the injector system comprising a heating element therein and at least one outlet port;
controllably applying energy from an energy source to the infill material via the heating element contemporaneously with flowing of the infill material through the injector system and before introducing the flowable infill material into the bone, the applied energy selectively increasing the viscosity of the infill material; and
introducing the flowable infill material having the selectively increased viscosity into the bone while controlling the viscosity of the flow of infill material through the controlled application of energy, the introduction of flowable infill material being controlled causing flowing of the flowable infill material, along a flow path through cancellous bone and interdigitating with cancellous bone, in the flow path wherein between an outer region of the flow path and the at least one outlet port in the flow path, the flow path comprises flowable infill material interdigitating with cancellous bone.

2. The method of claim 1, further comprising introducing the infill material into the interior region of the bone from a working end of an elongated introducer.

3. The method of claim 1, wherein the applied energy substantially accelerates polymerization of the infill material.

4. The method of claim 1, wherein the applied energy selectively increases the viscosity of infill material by at least 20%.

5. The method of claim 1, wherein the applied energy selectively alters a property selected from the group consisting of Young's modulus, percent elongation, surface hardness and durometer.

6. The method of claim 1, wherein the bone is a vertebra.

7. The method of claim 1, wherein the viscosity of the infill material is selectively increased to prevent extravasation in fractured cancellous bone.

8. The method of claim 1, wherein the infill material with increased viscosity has substantially reduced flowability upon being introduced into the bone.

9. The method of claim 1, wherein the infill material with increased viscosity is at least partially elastomeric upon being introduced into the bone.

10. The method of claim 1, wherein the application of energy is modulated by a controller.

11. The method of claim 10, wherein the application of energy is modulated in response to a monitored parameter of the infill material.

12. The method of claim 1, further comprising monitoring a parameter of the infill material.

13. The method of claim 12, wherein the parameter is at least one of temperature and impedance.

14. The method of claim 1, wherein the applied energy is changed over time.

15. The method of claim 1, wherein the energy source consists of at least one of a radiofrequency source, a resistive heat source, a laser source, a microwave source, a magnetic source and an ultrasound source.

16. The method of claim 1, wherein the infill material forms a flow impermeable surface on at least a portion of the infill material.

17. The method of claim 1, wherein introducing the infill material into the bone comprises introducing the infill material directly into the interior region of the bone.

18. The method of claim 17, wherein introducing the infill material directly into the interior region of the bone comprises injecting the infill material so that a majority of the infill material controllably interdigitates with a cancellous bone portion of the bone.

19. The method of claim 18, wherein introducing the infill material directly into the interior region of the bone comprises injecting the infill material so that all of the infill material controllably interdigitates with the cancellous bone portion of the bone.

20. The method of claim 1, wherein introducing the flowable infill material having the selectively increased viscosity into the bone includes introducing the flowable infill material into a bone portion having cancellous bone with marrow and blood vessels in spaces within cancellous bone.

21. A method for treating bone, comprising:
providing a flowable bone fill material;
controllably applying energy from an energy source to the bone fill material, wherein the application of energy selectively increases the viscosity of the bone fill material; and introducing a volume of the fill material having selectively increased viscosity into an interior of a bone while controlling the viscosity of the flow of flowable bone fill material through the controlled application of energy, the introduction of the volume of the bone fill material being controlled causing flowing of the flowable bone fill material, along a flow path that controllably interdigitates and permeates with a cancellous bone portion of the bone, the fill material being introduced along the flow path without previously creating a cavity which compresses or compacts the cancellous bone portion.

22. The method of claim 21, wherein the application of energy enhances polymerization of the bone fill material.

23. The method of claim 21, where in the application of energy increases the modulus of the fill material.

24. The method of claim 21, wherein the bone is a vertebra.

25. The method of claim 21, wherein the energy source is at least one of a radiofrequency source, a resistive heat source, a laser source, a microwave source, a magnetic source and an ultrasound source.

26. The method of claim 21, further comprising applying sufficient energy to the composition to substantially accelerate polymerization of the fill material.

27. The method of claim 21, wherein introducing the volume of fill material is done at least one of prior to or contemporaneously with the application of energy.

28. The method of claim 21, wherein applying energy includes applying energy to selected portions of the volume of fill material.

29. The method of claim 21, wherein the energy source applies energy to a conductive composition in at least one of a mono-polar manner and a bi-polar manner.

30. The method of claim 21, wherein the fill material includes a polymerizable component.

31. The method of claim 30, wherein the polymerizable component includes at least one of PMMA, monocalcium phosphate, tricalcium phosphate, calcium carbonate, calcium sulfate or hydroxyapatite.

32. The method of claim 21, further comprising contemporaneously controlling the application of energy with a controller.

33. The method of claim 21, wherein applying energy includes maintaining a specific power density in the fill material.

34. The method of claim 21, further comprising monitoring at least one parameter of the fill material.

35. The method of claim 34, wherein monitoring includes at least one of temperature monitoring and impedance monitoring.

36. The method of claim 21, wherein introducing the fill material supports or moves a cortical bone portion of the bone.

37. The method of claim 21, wherein introducing the volume of the fill material into the interior of the bone includes introducing the bone fill material so that a majority of the introduced bone fill material controllably interdigitates with the cancellous bone.

38. The method of claim 37, wherein introducing the fill material into the interior region of the bone comprises injecting the infill material so that all of the introduced fill material controllably interdigitates with the cancellous bone.

39. The method of claim 21, wherein the introduced volume of fill material controllably interdigitates and permeates with a cancellous bone meshwork.

40. A method for treating a vertebral body, comprising:
providing a bone fill material and an injector system having a portion positionable within the vertebral body, the injector system comprising a heating element therein and the bone fill material being loaded in the injector system;
positioning a portion of the injector system within the vertebral body;
controllably applying energy from an energy source to the bone fill material via the heating element before introducing the bone fill material into the bone, the applied energy selectively increasing viscosity of the bone fill material; and
introducing a volume of the bone fill material through an outlet port of the injector system into cancellous bone of the vertebral body while controlling the viscosity of the flow of bone fill material through the controlled application of energy, the introduction of the volume of the bone fill material being controlled causing flowing of the flowable bone fill material along a flow path that, controllably interdigitates with the cancellous bone and follows the flow path interdigitating and permeating through cancellous bone, an outer region of the flow path surrounding interdigitated cancellous bone located in the flow path between the outer region and the outlet port.

41. The method of claim 40, wherein controllably applying energy to the bone fill material increases the viscosity of the bone fill material by at least 100%.

42. The method of claim 40, wherein the viscosity of the infill material is selectively increased so as to inhibit extravasation in fractured cancellous bone.

43. The method of claim 40, wherein the application of energy is modulated by a controller.

44. The method of claim 43, wherein the application of energy is modulated in response to a monitored parameter of the bone fill material.

45. The method of claim 44, wherein the monitored parameter is at least one of temperature and impedance.

46. The method of claim 40, wherein the energy source consists of at least one of a radiofrequency source, a resistive heat source, a laser source, a microwave source, a magnetic source and an ultrasound source.

47. The method of claim 40, wherein introducing the volume of the bone fill material into cancellous bone of the vertebral body includes introducing the bone fill material so that a majority of the introduced bone fill material controllably interdigitates with the cancellous bone.

48. The method of claim 47, wherein introducing the fill material into the interior region of the bone comprises injecting the infill material so that all of the introduced fill material controllably interdigitates with the cancellous bone.

49. The method of claim 40, wherein the energy is applied to the bone fill material contemporaneously with the bone fill material flowing from the injector system into the cancellous bone.

50. The method of claim 40, wherein introducing the infill material directly into the interior region of the bone comprises injecting the infill material so that all of the infill material controllably interdigitates with the cancellous bone portion of the bone.

51. The method of claim 40, wherein introducing the fill material into the interior region of the bone comprises injecting the infill material so that all of the introduced fill material controllably interdigitates with the cancellous bone.

* * * * *

UNITED STATES PATENT AND TRADEMARK OFFICE
CERTIFICATE OF CORRECTION

PATENT NO. : 7,559,932 B2
APPLICATION NO. : 11/165652
DATED : July 14, 2009
INVENTOR(S) : Csaba Truckai et al.

It is certified that error appears in the above-identified patent and that said Letters Patent is hereby corrected as shown below:

On page 1, column 2, line 6, under OTHER PUBLICATIONS, delete "Verterbral" and insert -- Vertebral --, therefor.

At column 16, line 53, delete "chomophores" and insert -- chromophores --, therefor.

At column 17, line 64, under Claim 1, delete "material," and insert -- material --, therefor.

At column 17, line 66, under Claim 1, delete "bone," and insert -- bone --, therefor.

At column 17, line 66, under Claim 1, delete "path" and insert -- path, --, therefor.

At column 19, line 7, under Claim 21, delete "material," and insert -- material --, therefor.

At column 20, line 57, under Claim 50, delete "wherein introducing the infill material directly into the interior region of the bone comprises injecting the infill material so that all of the infill material controllably interdigitates with the cancellous bone portion of the bone" and insert -- wherein the fill material follows a flow path through cancellous bone without previously creating a cavity which compresses or compacts the cancellous bone --, therefor.

At column 20, line 62, under Claim 51, delete "wherein introducing the fill material into the interior region of the bone comprises injecting the infill material so that all of the introduced fill material controllably interdigitates with the cancellous bone" and insert -- wherein the bone fill material follows a flow path through cancellous bone having an outer region that completely surrounds interdigitated cancellous bone --, therefor.

Signed and Sealed this

Twenty-sixth Day of January, 2010

David J. Kappos
*Director of the United States Patent and Trademark Office*